(12) United States Patent
Lovett et al.

(10) Patent No.: US 7,570,997 B2
(45) Date of Patent: Aug. 4, 2009

(54) SUBCUTANEOUS CARDIAC RHYTHM MANAGEMENT WITH ASYSTOLE PREVENTION THERAPY

(75) Inventors: Eric G. Lovett, Roseville, MN (US); Adam W. Cates, Minneapolis, MN (US); Darrell Orvin Wagner, Isanti, MN (US); Mike Favet, San Jose, CA (US); Apurv Kamath, Solana Beach, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 347 days.

(21) Appl. No.: 10/820,642

(22) Filed: Apr. 8, 2004

(65) Prior Publication Data
US 2004/0215258 A1    Oct. 28, 2004

Related U.S. Application Data

(60) Provisional application No. 60/462,272, filed on Apr. 11, 2003.

(51) Int. Cl.
*A61N 1/362* (2006.01)
(52) U.S. Cl. .................... 607/14; 67/4; 67/10; 67/63
(58) Field of Classification Search .............. None
See application file for complete search history.

(56) References Cited

U.S. PATENT DOCUMENTS

| | | | |
|---|---|---|---|
| 4,312,355 A | 1/1982 | Funke | |
| 4,562,841 A | 1/1986 | Brockway et al. | |
| 4,693,253 A | 9/1987 | Adams | |
| 4,784,162 A | 11/1988 | Ricks et al. | |
| 4,827,943 A | 5/1989 | Bornn et al. | |
| 4,940,054 A | 7/1990 | Grevis et al. | |
| 4,953,551 A | 9/1990 | Mehra et al. | |
| 5,003,975 A | 4/1991 | Hafelfinger et al. | |
| 5,014,698 A * | 5/1991 | Cohen | 607/4 |
| 5,036,849 A | 8/1991 | Hauck et al. | |
| 5,074,301 A * | 12/1991 | Gill | 607/4 |
| 5,133,353 A | 7/1992 | Hauser | |
| 5,156,157 A | 10/1992 | Valenta, Jr. et al. | |
| 5,170,784 A | 12/1992 | Ramon et al. | |
| 5,179,945 A | 1/1993 | Van Hofwegen et al. | |

(Continued)

FOREIGN PATENT DOCUMENTS

EP    1234597    8/2002

(Continued)

OTHER PUBLICATIONS

Renee Hartz et al., *New Approach to Defibrillator Insertion*. J. Thoracic Cardiovascular Surgery. vol. 97, pp. 920-922 (1989).

(Continued)

*Primary Examiner*—Kennedy J Schaetzle
(74) *Attorney, Agent, or Firm*—Hollingsworth & Funk, LLC

(57) ABSTRACT

Systems and methods provide for sensing of cardiac activity from a subcutaneous, non-intrathoracic location, and detecting a cardiac condition necessitating treatment in response to the sensed cardiac activity. One of a number of cardiac therapies may be selectively delivered to treat the detected cardiac condition, such cardiac therapies including at least a tachycardia therapy, a bradycardia therapy, and an asystole prevention therapy.

61 Claims, 12 Drawing Sheets

U.S. PATENT DOCUMENTS

| | | |
|---|---|---|
| 5,188,106 A | 2/1993 | Nappholz et al. |
| 5,203,348 A | 4/1993 | Dahl et al. |
| 5,209,229 A | 5/1993 | Gilli |
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,306,293 A | 4/1994 | Zacouto |
| 5,313,953 A | 5/1994 | Yomtov et al. |
| 5,314,430 A | 5/1994 | Bardy |
| 5,314,459 A | 5/1994 | Swanson et al. |
| 5,318,593 A | 6/1994 | Duggan |
| 5,318,594 A | 6/1994 | Limousin et al. |
| 5,318,597 A | 6/1994 | Hauck et al. |
| 5,331,966 A | 7/1994 | Bennett et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,187 A | 2/1995 | Freeman |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,417,717 A | 5/1995 | Salo et al. |
| 5,439,482 A | 8/1995 | Adams et al. |
| 5,441,518 A | 8/1995 | Adams et al. |
| 5,468,254 A | 11/1995 | Hahn et al. |
| 5,527,345 A | 6/1996 | Infinger |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,601,607 A | 2/1997 | Adams |
| 5,603,331 A | 2/1997 | Heemels et al. |
| 5,603,732 A | 2/1997 | Dahl et al. |
| 5,606,969 A | 3/1997 | Butler et al. |
| 5,607,385 A | 3/1997 | Francischelli et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,724,984 A | 3/1998 | Arnold et al. |
| 5,782,883 A | 7/1998 | Kroll et al. |
| 5,797,967 A | 8/1998 | KenKnight |
| 5,814,079 A * | 9/1998 | Kieval ............................ 607/4 |
| 5,827,326 A | 10/1998 | Kroll et al. |
| 5,836,987 A | 11/1998 | Baumann et al. |
| 5,855,593 A | 1/1999 | Olson et al. |
| 5,869,970 A | 2/1999 | Palm et al. |
| 5,895,414 A | 4/1999 | Sanchez-Zambrano |
| 5,916,243 A | 6/1999 | KenKnight et al. |
| 5,919,141 A | 7/1999 | Money et al. |
| 5,957,956 A | 9/1999 | Kroll et al. |
| 5,961,446 A | 10/1999 | Beller et al. |
| 5,961,450 A | 10/1999 | Merchant et al. |
| 6,044,298 A | 3/2000 | Salo et al. |
| 6,050,940 A | 4/2000 | Braun et al. |
| 6,055,454 A | 4/2000 | Heemels |
| 6,126,611 A | 10/2000 | Bourgeois et al. |
| 6,141,581 A | 10/2000 | Olson et al. |
| 6,148,230 A | 11/2000 | KenKnight |
| 6,205,357 B1 | 3/2001 | Ideker et al. |
| 6,221,011 B1 | 4/2001 | Bardy |
| 6,259,947 B1 | 7/2001 | Olson et al. |
| 6,270,475 B1 | 8/2001 | Bestetti et al. |
| 6,277,072 B1 | 8/2001 | Bardy |
| 6,280,380 B1 | 8/2001 | Bardy |
| 6,280,462 B1 | 8/2001 | Hauser et al. |
| 6,303,270 B1 | 10/2001 | Flaim et al. |
| 6,304,773 B1 | 10/2001 | Taylor |
| 6,306,088 B1 | 10/2001 | Krausman |
| 6,312,378 B1 | 11/2001 | Bardy |
| 6,314,319 B1 | 11/2001 | Kroll et al. |
| 6,336,903 B1 | 1/2002 | Bardy |
| 6,351,670 B1 | 2/2002 | Kroll |
| 6,358,203 B2 | 3/2002 | Bardy |
| 6,368,284 B1 | 4/2002 | Bardy |
| 6,375,614 B1 | 4/2002 | Braun et al. |
| 6,398,728 B1 | 6/2002 | Bardy |
| 6,409,675 B1 | 6/2002 | Turcott |
| 6,415,174 B1 | 7/2002 | Bebehani et al. |
| 6,438,410 B2 | 8/2002 | Hsu et al. |
| 6,440,066 B1 | 8/2002 | Bardy |
| 6,442,433 B1 | 8/2002 | Linberg |
| 6,450,957 B1 | 9/2002 | Yoshimi |
| 6,454,708 B1 | 9/2002 | Ferguson et al. |
| 6,480,733 B1 | 11/2002 | Turcott |
| 6,487,443 B2 | 11/2002 | Olson et al. |
| 6,491,639 B1 | 12/2002 | Turcott |
| 6,512,940 B1 | 1/2003 | Brabec et al. |
| 6,522,915 B1 | 2/2003 | Ceballos et al. |
| 6,556,862 B2 | 4/2003 | KenKnight et al. |
| 6,564,106 B2 | 5/2003 | Guck et al. |
| 6,574,507 B1 | 6/2003 | Bonnet |
| 6,589,188 B1 | 7/2003 | Street et al. |
| 6,600,949 B1 | 7/2003 | Turcott |
| 6,607,509 B2 | 8/2003 | Bobroff et al. |
| 6,615,083 B2 | 9/2003 | Kupper |
| 6,618,618 B2 | 9/2003 | Kalgren et al. |
| 6,622,046 B2 | 9/2003 | Fraley et al. |
| 6,625,491 B2 | 9/2003 | Ripart |
| 6,628,986 B1 | 9/2003 | Mouchawar et al. |
| 6,704,590 B2 | 3/2004 | Haldeman |
| 6,708,058 B2 | 3/2004 | Kim et al. |
| 6,892,095 B2 | 5/2005 | Salo |
| 6,895,273 B2 | 5/2005 | Seim et al. |
| 6,922,589 B2 | 7/2005 | Stahmann et al. |
| 7,189,204 B2 | 3/2007 | Ni et al. |
| 7,252,640 B2 | 8/2007 | Ni et al. |
| 7,396,333 B2 | 7/2008 | Stahmann et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1* | 6/2002 | Heinrich et al. ................. 607/9 |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107553 A1 | 8/2002 | Hill et al. |
| 2002/0107559 A1 | 8/2002 | Sanders et al. |
| 2002/0120299 A1 | 8/2002 | Ostroff et al. |

| | | | |
|---|---|---|---|
| 2003/0004546 | A1 | 1/2003 | Casey |
| 2003/0004547 | A1* | 1/2003 | Owen et al. .................. 607/5 |
| 2003/0004552 | A1 | 1/2003 | Plombon et al. |
| 2003/0023175 | A1 | 1/2003 | Arzbaecher et al. |
| 2003/0036778 | A1 | 2/2003 | Ostroff et al. |
| 2003/0045904 | A1 | 3/2003 | Bardy et al. |
| 2003/0069609 | A1 | 4/2003 | Thompson |
| 2003/0088278 | A1 | 5/2003 | Bardy et al. |
| 2003/0088279 | A1 | 5/2003 | Rissmann et al. |
| 2003/0088280 | A1 | 5/2003 | Ostroff |
| 2003/0088281 | A1 | 5/2003 | Ostroff et al. |
| 2003/0088282 | A1 | 5/2003 | Ostroff |
| 2003/0088283 | A1 | 5/2003 | Ostroff |
| 2003/0088286 | A1 | 5/2003 | Ostroff et al. |
| 2003/0097153 | A1 | 5/2003 | Bardy et al. |
| 2003/0114887 | A1 | 6/2003 | KeKnight |
| 2003/0163169 | A1 | 8/2003 | Hill et al. |
| 2003/0204216 | A1 | 10/2003 | Ries et al. |
| 2003/0212436 | A1 | 11/2003 | Brown |
| 2004/0064177 | A1 | 4/2004 | Bardy et al. |
| 2004/0172066 | A1* | 9/2004 | Wagner et al. ................. 607/4 |
| 2004/0215240 | A1 | 10/2004 | Lovett et al. |
| 2004/0215258 | A1* | 10/2004 | Lovett et al. .................. 607/9 |
| 2004/0230229 | A1 | 11/2004 | Lovett et al. |
| 2004/0230230 | A1 | 11/2004 | Lindstrom |
| 2005/0004615 | A1 | 1/2005 | Sanders |
| 2005/0043652 | A1 | 2/2005 | Lovett et al. |
| 2006/0047333 | A1 | 3/2006 | Tockman et al. |

FOREIGN PATENT DOCUMENTS

| | | |
|---|---|---|
| EP | 1304137 | 4/2003 |
| WO | WO 92/20402 | 11/1992 |
| WO | WO0009206 | 2/2000 |

OTHER PUBLICATIONS

Theofilos M. Kolettis, MD, PhD et al., *Submammary Implantation of a Cardioverter-Defibrillator with a Nonthoracotomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at col. 778, p. B83).

Stirbis et al., *Optimizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol.24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

Press Release Biotronik 2003. *Biotronik Announces FDA Approval of the Low-Cost Cardiac Airbag™ Implantable Cardioverter Defibrillator System*. Portland, Oregon. cardiac-airbag@biotronikusa.com. 2 pages (May 15, 2003).

Biotronik © 2003 Website product literature. *Cardiac Airbag™ / Meeting the Needs of the At Risk Patient*. 3 pages.

Altamura et al., Emergency Cardiac Pacing for Severe Bradycardia, PACE, vol. 13, pp. 2038-2043, Dec. 1990, Part II.

www.medtronic.com/reveal/new.html. Medtronic, Inc. 2001. New Diagnostic Tool—Reveal® Insertable Loop Recorder. Medtronic Website, updated Jul. 12, 2001 (3 sheets). Printed from the internet Sep. 16, 2008.

Satoh et al., Role of Hypoxic Drive in Regulation of Postapneic Ventilation During Sleep in Patients with Obstructive Sleep Apnea, Am Rev Respir Dis., vol. 143(3), Mar. 1991, Abstract only.

* cited by examiner

SUBCUTANEOUS CARDIAC RHYTHM MANAGEMENT WITH ASYSTOLE PREVENTION THERAPY

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to medical devices and, more particularly, to implantable or partially implantable subcutaneous systems and methods for detecting cardiac activity and treating adverse cardiac events or conditions.

BACKGROUND OF THE INVENTION

The healthy heart produces regular, synchronized contractions. Rhythmic contractions of the heart are normally initiated by the sinoatrial (SA) node, which are specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating the arrhythmias described above.

Implantable cardioverter/defibrillators (ICDs) have been used as an effective treatment for patients with serious cardiac arrhythmias. For example, a typical ICD includes one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. The primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to medical devices and methods that provide for a multiplicity of deliverable cardiac therapies using one or more components configured for subcutaneous, non-intrathoracic placement in a patient. According to one embodiment, a system of the present invention includes detection circuitry, energy delivery circuitry, and a controller. The energy delivery circuitry is capable of delivering a number of cardiac therapies including at least a tachycardia therapy, a bradycardia therapy, and an asystole prevention therapy. One or more electrodes of the system are configured for subcutaneous, non-intrathoracic placement and for coupling to the detection circuitry and energy delivery circuitry. The controller is coupled to the detection circuitry and energy delivery circuitry. The controller, in response to a cardiac condition requiring treatment, coordinates delivery of a selected one of the tachycardia, bradycardia, and asystole prevention therapies.

In various embodiments, a housing is configured for implantation in the patient, and one or more of the detection circuitry, energy delivery circuitry, and controller is situated in the housing. One or more of the electrodes may be disposed in or on the housing. One or more of the electrodes may also be supported on a lead or by an electrode support extending from the housing. For example, the system may include one or more subcutaneous, non-intrathoracic electrode arrays that support one or more electrodes. In other embodiments, the housing may define a unitary structure, such that the electrodes are mounted on or in the housing. The housing may, for example, have an arcuate shape.

In various embodiments, the housing is configured for patient-external placement, and one or more of the detection circuitry, energy delivery circuitry, and controller is situated in the housing. The housing may include one or more electrodes coupled to the detection circuitry and energy delivery circuitry. The system may further include one or more surface electrodes configured for coupling to the detection circuitry and energy delivery circuitry. In a patient-external configuration, a coupling arrangement may be used and configured to couple and de-couple the one or more implantable and/or surface electrodes to and from the detection circuitry and energy delivery circuitry.

In certain embodiments, the multiplicity of deliverable cardiac therapies may include at least some of a bradycardia pacing therapy, a cardiac resynchronization therapy, an anti-tachycardia pacing therapy, a defibrillation therapy, a rate smoothing pacing therapy, and/or a sub-threshold stimulation therapy.

In accordance with other embodiments, a method of the present invention involves sensing cardiac activity from a subcutaneous, non-intrathoracic location, and detecting a cardiac condition necessitating treatment in response to the sensed cardiac activity. The method further involves delivering one of a number of cardiac therapies to treat the detected cardiac condition, such cardiac therapies including at least a tachycardia therapy, a bradycardia therapy, and an asystole prevention therapy. Energy for the cardiac therapies may be provided from a patient-external source or a patient-internal source.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
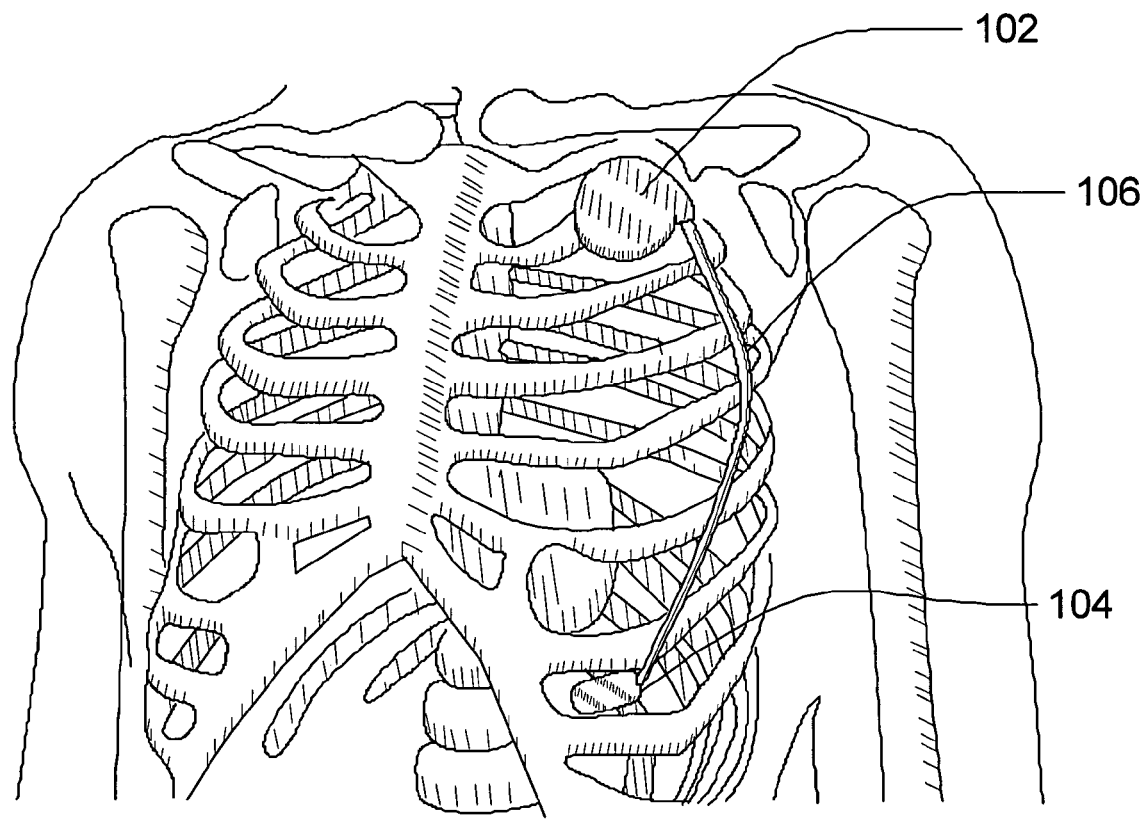
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac stimulator may be implemented to include one or more of the advantageous features and/or processes described below. It is intended that such a stimulator or other implanted or partially implanted device need not include all of the features described herein, but may be implemented to include selected features that provide for unique structures and/or functionality. Such a device may be implemented to provide a variety of therapeutic or diagnostic functions.

Embodiments of the present invention are directed to a cardiac stimulation device, at least some elements of which are configured for subcutaneous, non-intrathoracic placement in the body. The cardiac stimulation device is configured to sense cardiac activity and detect adverse cardiac events or conditions, such as cardiac arrhythmia (e.g., bradycardia, tachycardia, fibrillation), post-shock asystole, and poor cardiac output, for example. The cardiac stimulation device is configured to deliver a number of therapies. Such therapies may include, but are not limited to, tachycardia therapy, including defibrillation therapy, a bradycardia therapy, and an asystole prevention therapy. In response to detecting an adverse cardiac event or condition requiring treatment, the cardiac stimulation device determines which of several available therapies is appropriate to treat the subject event or condition and delivers an appropriate therapy.

Various embodiments are directed to cardiac stimulation devices that can be implemented to provide transthoracic, subcutaneous pacing for an integrated approach to asystole prevention, anti-bradycardia pacing, and anti-tachycardia pacing, for example. Subcutaneous transthoracic pacing may be employed for other applications in which endo-/epi-cardial pacing has traditionally been used. For example, subcutaneous pacing can be used to induce tachyarrhythmias. Such cardiac stimulation devices can be used to deliver monophasic, biphasic, and multiphasic (e.g., triphasic) waveforms useful to elicit cardiac stimulation.

Subcutaneous transthoracic pacing can be used as part of a cardiac rhythm management system for asystole, anti-bradycardia, and anti-tachycardia applications. Various subcutaneous transthoracic pacing therapies may be combined with subcutaneous transthoracic defibrillation and cardioversion therapies to provide for an integrated, comprehensive approach to cardiac rhythm management. Systems incorporating some or all of these capabilities can be implanted subcutaneously or reside outside the body in cases of temporary need.

Subcutaneous transthoracic pacing devices according to embodiments of the present invention can pave the way for new directions in implanted rhythm management systems. To reduce complexity of implant, such devices may use subcutaneous transthoracic stimulation for pacing and defibrillation purposes. Such devices can also provide for new directions in external cardiac rhythm management systems. Subcutaneous transthoracic pacing may be better tolerated than conventional transcutaneous transthoracic pacing. In one configuration, for example, an external pulse generator may be connected to subcutaneous electrodes for purposes of delivering various types of transthoracic pacing, such as those discussed above and below. The combination of an external pulse generator and subcutaneous electrodes may result in better patient acceptance of therapy in cases where temporary support is needed.

From a standpoint of implanted devices, a system or device that employs subcutaneous transthoracic pacing allows for the development of implanted cardiac rhythm management systems that operate from a subcutaneous location rather than conventional transvenous or epicardial environments. For external systems, this approach may resolve cases where patients do not tolerate transcutaneous stimulation well.

In various embodiments, a cardiac stimulation device may be configured to deliver cardiac therapies which may include, for example, a cardiac resynchronization therapy, an anti-tachycardia pacing therapy, a defibrillation therapy, a rate smoothing or regularization pacing therapy, a sub-threshold stimulation therapy, a subcutaneous non-intrathoracic pacing, cardioversion or defibrillation therapy, an intrathoracic pacing, cardioversion or defibrillation therapy, or a combined intrathoracic/non-intrathoracic pacing, cardioversion or defibrillation therapy. In certain embodiments, the cardiac stimulation device may be configured to include only subcutaneous, non-intrathoracic components, including subcutaneous, non-intrathoracic electrodes (can electrodes and/or electrodes separate from the device housing). In other embodiments, the cardiac stimulation device may be configured to include subcutaneous, non-intrathoracic components and intrathoracic components, such as one or more epicardial, endocardial or transvenous leads/electrodes.

Various embodiments may also include one or more non-electrophysiologic sensors for sensing cardiac or cardiac related activity, or sensors for sensing other physiologic conditions. Such non-electrophysiologic sensors may include, for example, optical blood sensors (oximetery sensors and/or photoplythesmographic sensors), accelerometers, transthoracic impendence sensors, pressure sensors, ultrasonic sensors, and temperatures sensors, among others. These sensors may be implantable, external, or partially implantable in the body. Such sensors may be employed to enhance or verify assessment and detection of a cardiac signal in the presence of noise or electrocardiographic artifacts, and/or to enhance detection and discrimination of cardiac arrhythmias. Embodiments of the present invention may incorporate one or more features disclosed in commonly owned, co-pending U.S. patent application Ser. No. 10/784,478 filed Feb. 23, 2004, now U.S. Publication No. 2005/0119708 and in U.S. patent application Ser. No. 10/804,471, filed Mar. 19, 2004, now U.S. Publication No. 2004/0230129; U.S. patent application Ser. No. 10/816,464, filed Apr. 1, 2004, now U.S. Publication No. 2004/0220633; and U.S. patent application Ser. No. 10/817,749, filed Apr. 2, 2004, now U.S. Publication No. 2004/0220629, and in U.S. Pat. Nos. 6,409,675; 6,415,174; 6,480,733; and 6,491,639, all of which are hereby incorporated herein by reference in their respective entireties.

Various embodiments are directed to a cardiac stimulation system that includes an external therapy device and one or more internal leads/electrodes. The internal leads/electrodes are preferably configured for subcutaneous, non-intrathoracic placement in the body. In addition, the internal leads/electrodes may include one or more epicardial, endocardial or transvenous leads/electrodes. The external therapy device is configured to detect cardiac activity and adverse cardiac events or conditions. The external therapy device is configured to deliver a number of therapies, which may include, but are not limited to, tachycardia therapy, including defibrillation therapy, a bradycardia therapy, and an asystole prevention therapy. In response to detecting an adverse cardiac event or condition requiring treatment, the external therapy cardiac stimulation device determines which of the several available therapies is appropriate to treat the subject event or condition and delivers an appropriate therapy.

With regard to embodiments directed to internal cardiac stimulation devices, one such device is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or sub-clavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, the ITCS device may include one or more leads incorporating electrodes configured for positioning in direct contact with the heart, great vessel or coronary vasculature, such as via one or more leads implanted by use of conventional transvenous or epicardial delivery approaches. An ITCS device of this configuration may be viewed as a hybrid system that is capable of operating in numerous modes, including intrathoracic modes, subcutaneous non-intrathoracic modes, or a combination of these modes (operating in parallel or sequentially). In general, an ITCS device employing intrathoracic leads/electrodes may perform a variety of sensing, detection, diagnostics, and therapy operations using intrathoracic electrodes, subcutaneous non-intrathoracic electrodes, or a combination of these electrodes. Inclusion of intrathoracic electrodes may provide for enhanced cardiac management features, including monitoring, pacing, defibrillation, resynchronization, and sub-threshold stimulation features. An ITCS device implemented according to this approach may incorporate structures and functions disclosed in commonly owned, co-pending U.S. patent application Ser. No. 10/462,001 filed Jun. 13, 2003, now U.S. Publication No. 2004/0230229 and in U.S. Pat. No. 5,331,966, which are hereby incorporated herein by reference.

By way of example, an ITCS device employing one or more intrathoracic leads/electrodes may be configured to provide multichamber or multisite pacing for treatment of contractile dysfunction, while concurrently treating bradycardia and tachycardia. An ITCS device of this configuration can operate as a cardiac function management device, or CFM device, to improve pumping function by altering heart chamber contraction sequences while maintaining pumping rate and rhythm. Various ITCS device embodiments described herein may be used in connection with congestive heart failure monitoring, diagnosis, and/or therapy. Methods, structures, and/or techniques directed to CHF treatment, such as those involving dual-chamber or bi-ventricular pacing/therapy, cardiac resynchronization therapy, cardiac function optimization, or other CHF related methodologies, can be incorporated in an ITCS device of the present invention and include features of one or more of the following references: commonly owned U.S. patent application Ser. No. 10/270, 035, filed Oct. 11, 2002, now U.S. Publication No. 2003/0130702 and U.S. Pat. Nos. 6,411,848; 6,285,907; 4,928,688; 6,459,929; 5,334,222; 6,026,320; 6,371,922; 6,597,951; 6,424,865; and 6,542,775, each of which is hereby incorporated herein by reference.

An ITCS device employing one or more intrathoracic leads/electrodes may be configured to provide a rate smoothing or regularization pacing therapy. Rate smoothing provides a measure of control over the rate of change of the ventricular pacing rate. According to one approach, the rate of change of the ventricular pacing rate is preferably controlled on a cycle-to-cycle basis so as to maintain the rate of change within a programmed percentage of the previous cycle's rate. This function is achieved via the comparison of the ventricular pacing rate for each cycle to a "rate window" or percentage of the period for the previous cardiac cycle so as to ensure that the period of the pacing pulses is constrained from cycle to cycle by the limits defined by the rate window. Controlling when and under what cardiac conditions to turn on/off or adjust the parameters for a rate smoothing program may be highly advantageous. This control allows the rate smoothing to be deactivated when use of rate smoothing would be detrimental, or constraining, to a patient's need for rapid heart rate acceleration or deceleration. Furthermore, by selectively turning rate smoothing off or adjusting rate smoothing parameters, the number of pacing pulses delivered to a patient may be reduced. Exemplary structures and methods for implementing a rate smoothing pacing therapy in an ITCS device of the present invention are disclosed in commonly owned U.S. Pat. No. 6,501,987, which is hereby incorporated herein by reference.

By way of further example, an ITCS device employing one or more intrathoracic leads/electrodes may be configured to provide sub-threshold electrical stimulation to the heart for a variety of purposes, including enhancing cardiac contractility and/or cardiac contractility modulation, and automaticity through sub-threshold currents. For example, biphasic electrical stimulation may be administered to the cardiac muscle, such that the anodal stimulation component augments cardiac contractility by hyperpolarizing the tissue prior to excitation, leading to faster impulse conduction, more intracellular calcium release, and overall superior cardiac contraction. The cathodal stimulation component of the biphasic electrical stimulation provides for effective cardiac stimulation at a lower voltage level than would be required with anodal stimulation alone. This in turn, extends pacemaker battery life and reduces tissue damage. An ITCS device of the present invention may incorporate features and functionality to facilitate sub-threshold biphasic electrical stimulation as disclosed in U.S. Pat. No. 6,341,235, which is hereby incorporated herein by reference.

An ITCS device may incorporate an electrical stimulation therapy such that the magnitude of an anodal phase of an electrical stimulation waveform does not exceed the maximum sub-threshold amplitude. The anodal phase of the electrical stimulation waveform serves to precondition the stimulated myocardium, thereby lowering the excitation threshold such that a cathodal stimulation of lesser intensity than normal will produce depolarization leading to contraction. An ITCS device of the present invention may incorporate features and functionality to facilitate sub-threshold electrical stimulation as disclosed in U.S. Pat. No. 6,411,845, which is hereby incorporated herein by reference.

In a further implementation, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart. Examples of useful subcutaneous electrodes, electrode arrays, and orientations of same are described in commonly owned U.S. patent application Ser. No. 10/738,608 filed Dec. 17, 2003, now U.S. Publication No. 2004/0230243, and U.S. patent application Ser. No. 10/465,520 filed Jun. 19, 2003, now U.S. Publication No. 2004/0230230, which are hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Exemplary ICD circuitry, structures and functionality, aspects of which may be incorporated in an ITCS device of a type described herein (e.g., a purely subcutaneous implementation or a hybrid implementation), are disclosed in commonly owned U.S. Pat. Nos. 5,133,353; 5,179,945; 5,314,459; 5,318,597; 5,331,966; 5,620,466; 5,662,688, and 6,522,915, and in U.S. patent application Ser. No. 10/011,506, filed Nov. 5, 2001, now U.S. Publication No. 2002/0107544, which are hereby incorporated herein by reference in their respective entireties.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from signal separation, are disclosed in commonly owned U.S. Pat. Nos. 4,562,841; 5,036,849; 5,284,136; 5,376,106; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device in accordance with the present invention may implement diagnostic and/or monitoring functions as well as provide cardiac stimulation therapy. Exemplary cardiac monitoring circuitry, structures and functionality, aspects of which may be incorporated in an ITCS device of a type that may benefit from signal separation in accordance with the present invention, are disclosed in commonly owned U.S. Pat. Nos. 5,313,953; 5,388,578; and 5,411,031, which are hereby incorporated herein by reference in their respective entireties.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 1B:
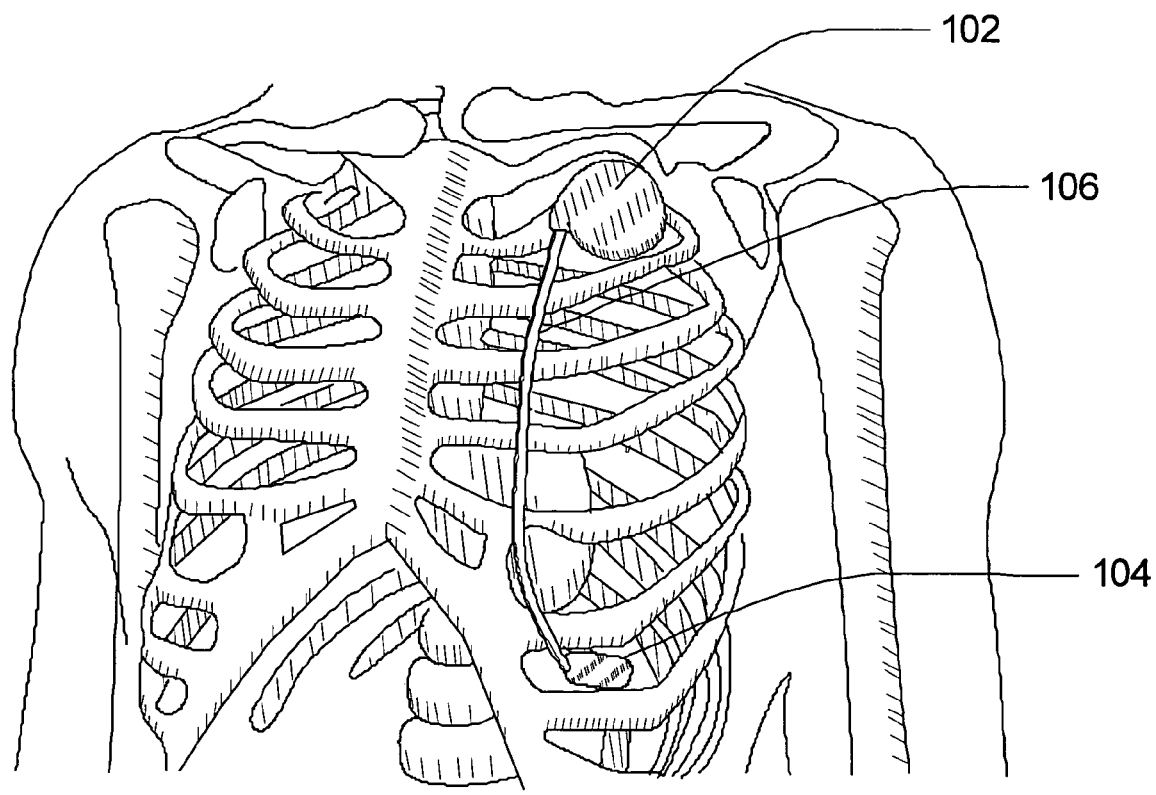

Referring now to FIGS. 1A and 1B of the drawings, there is shown a configuration of an ITCS device having components implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible and has a construction similar to conventional implantable, medical electrical leads (e.g., defibrillation leads or combined defibrillation/pacing leads). In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes an electrode support assembly, such as a rigid or semi-rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and subcutaneous electrode 104 is provided in cases where the elongated structure is formed from an electrically conductive material, such as metal.

In one configuration, the electrode support assembly and the housing 102 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 102. The electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the electrode support assembly and housing 102. The header block arrangement may be provided on the housing 102 or the electrode support assembly. Alternatively, a mechanical/electrical coupler may be used to establish mechanical and electrical connections between the electrode support assembly and housing 102. In such a configuration, a variety of different electrode support assemblies of varying shapes, sizes, and electrode configurations may be made available for physically and electrically connecting to a standard ITCS device housing 102.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst subcutaneous electrodes 104.

An ITCS device may incorporate circuitry, structures and functionality of the subcutaneous implantable medical devices disclosed in commonly owned U.S. Pat. Nos. 5,203, 348; 5,230,337; 5,360,442; 5,366,496; 5,391,200; 5,397,342; 5,545,202; 5,603,732; and 5,916,243, which are hereby incorporated herein by reference in their respective entireties.

Figure 1C:
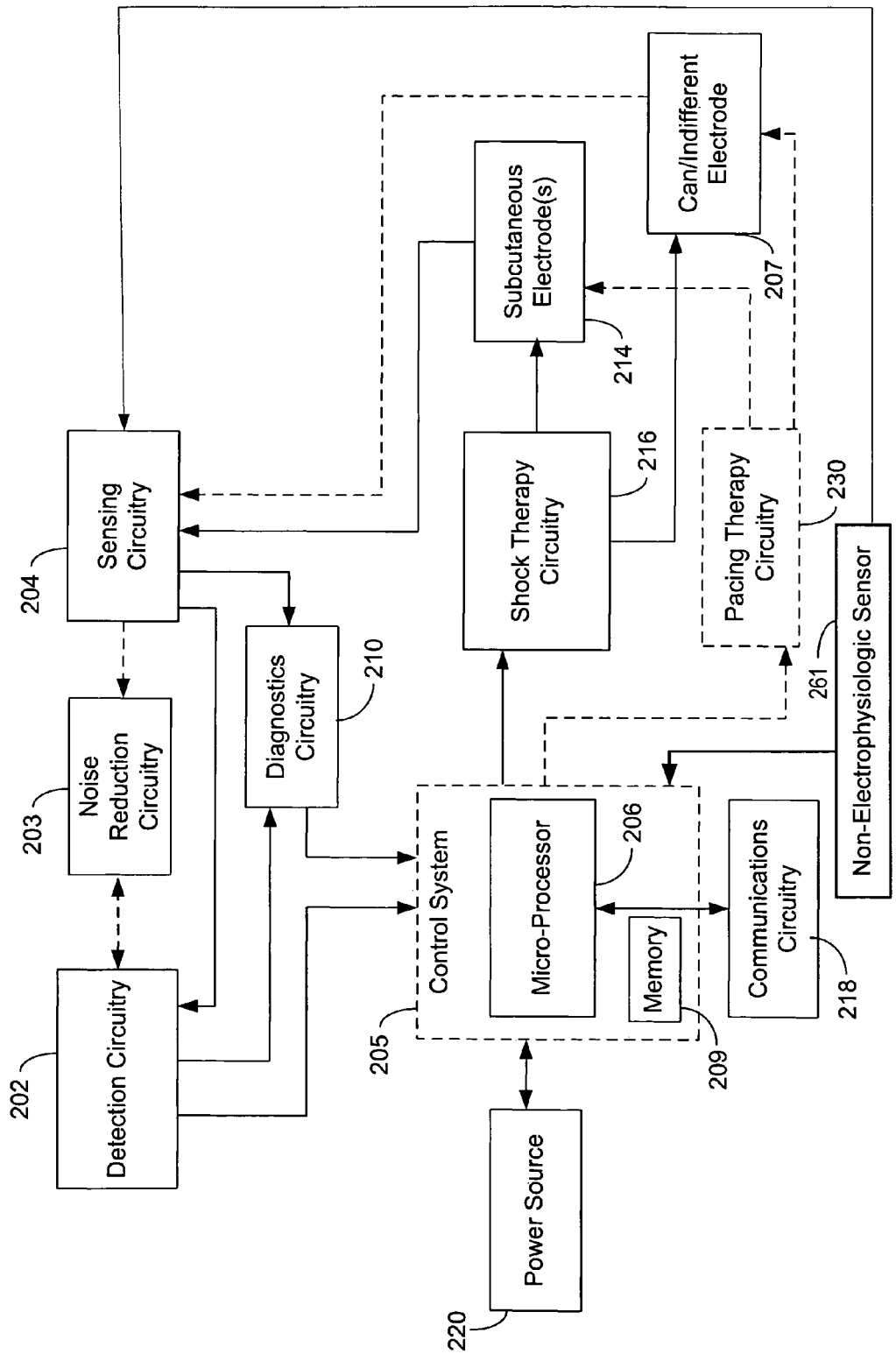
FIG. 1C is a block diagram illustrating various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythrmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. As such, unipolar, bipolar, or combined unipolar/bipolar electrode configurations as well as multi-element electrodes and combinations of noise canceling and standard electrodes may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise before signals are sent to the detection circuitry 202.

Noise reduction circuitry 203 may also be incorporated after the sensing circuitry 204 or detection circuitry 202 in cases where high power or computationally intensive noise reduction algorithms are required. The noise reduction circuitry 203, by way of amplifiers used to perform operations with the electrode signals, may also perform the function of the sensing circuitry 204. Combining the functions of sensing circuitry 204, detection circuitry 202, and/or noise reduction circuitry 203 may be useful to minimize the necessary componentry and lower the power requirements of the system.

In the illustrative configuration shown in FIG. 1C, the detection circuitry 202 is coupled to, or otherwise incorporates, noise reduction circuitry 203. The noise reduction circuitry 203 operates to improve the signal-to-noise ratio (SNR) of sensed cardiac signals by removing noise content of the sensed cardiac signals introduced from various sources. Typical types of transthoracic cardiac signal noise includes electrical noise and noise produced from skeletal muscles, for example.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Exemplary arrhythmia detection and discrimination circuitry, structures, and techniques, aspects of which may be implemented by an ITCS device of a type that may benefit from signal separation in accordance with the present invention, are disclosed in commonly owned U.S. Pat. Nos. 5,301,677 and 6,438,410, which are hereby incorporated herein by reference in their respective entireties.

The detection circuitry 202 communicates cardiac signal information to the control system 205. Memory circuitry 209 of the control system 205 contains parameters for operating in various sensing, defibrillation, and, if applicable, pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Exemplary ICD high energy delivery circuitry, structures and functionality, aspects of which may be incorporated in an ITCS device of a type described herein are disclosed in commonly owned U.S. Pat. Nos. 5,372,606; 5,411,525; 5,468,254; and 5,634,938, and in U.S. patent application Ser. No. 10/011,947, filed Nov. 5, 2001, now U.S. Pat. No. 7,039,459, which are hereby incorporated herein by reference in their respective entireties.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies may be useful in a transthoracic cardiac monitoring and/or stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C is configured to receive signals from one or more physiologic and/or non-physiologic sensors in accordance with embodiments of the present invention. Depending on the type of sensor employed, signals generated by the sensors may be communicated to transducer circuitry coupled directly to the detection circuitry 202 or indirectly via the sensing circuitry 204. It is noted that certain sensors may transmit sense data to the control system 205 without processing by the detection circuitry 202.

Non-electrophysiological cardiac sensors may be coupled directly to the detection circuitry 202 or indirectly via the sensing circuitry 204. Non-electrophysiological cardiac sensors sense cardiac activity that is non-electrophysiological in nature. Examples of non-electrophysiological cardiac sensors include blood oxygen sensors, transthoracic impedance sensors, blood volume sensors, acoustic sensors and/or pressure transducers, and accelerometers. Signals from these sensors are developed based on cardiac activity, but are not derived directly from electrophysiological sources (e.g., R-waves or P-waves). A non-electrophysiological cardiac sensor 261, as is illustrated in FIG. 1C, may be connected to one or more of the sensing circuitry 204, detection circuitry 202 (connection not shown for clarity), and the control system 205. An ITCS device of the present invention may incorporate non-electrophysiological cardiac sensors and rhythm detection techniques disclosed in various U.S. Patents and Applications incorporated herein by reference, particularly in the commonly owned US Patent Applications identified above and in U.S. Pat. Nos. 6,491,639; 6,480,733; 6,415,174; and 6,409,675, all of which are hereby incorporated herein by reference in their respective entireties.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external to the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. To facilitate non-invasive power source charging, the communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
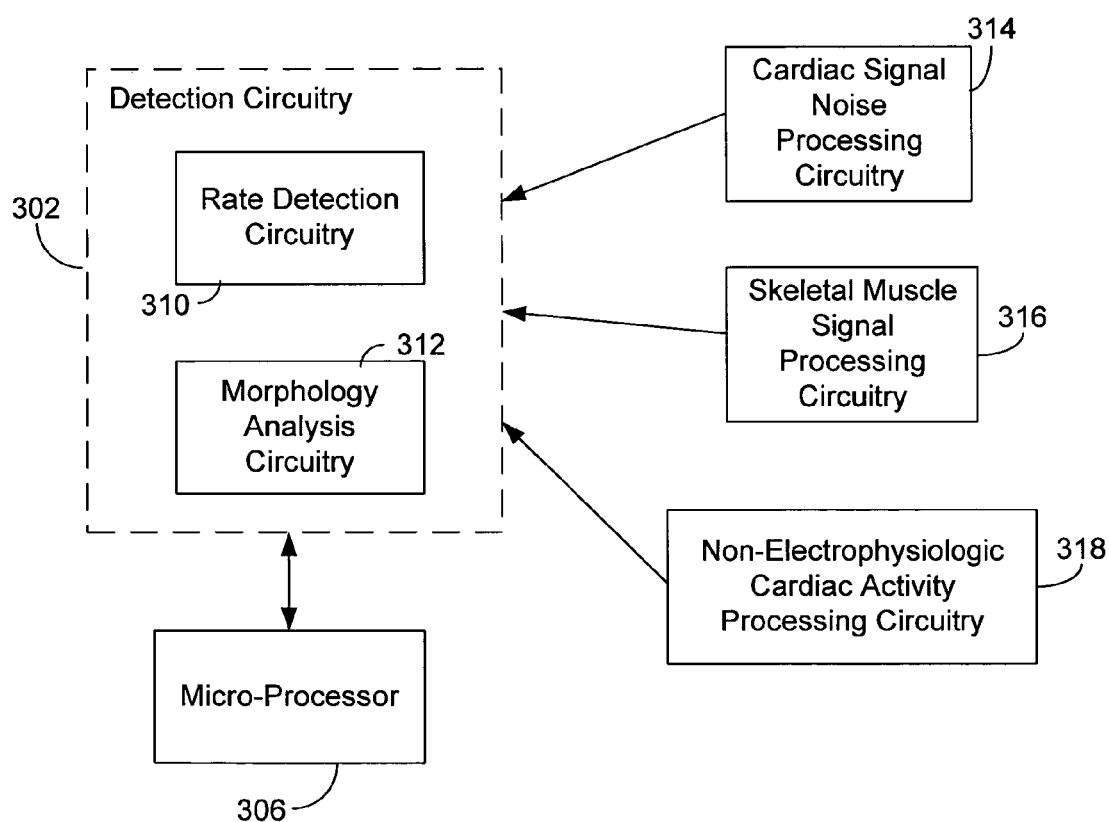
FIG. 1D is a block diagram illustrating various processing and detection components of a transthoracic cardiac sensing and/or stimulation device in accordance with an embodiment of the present invention.

FIG. 1D illustrates a configuration of detection circuitry 302 of an ITCS device, which includes one or both of rate detection circuitry 310 and morphological analysis circuitry 312. Detection and verification of arrhythmias may be accomplished using rate-based discrimination algorithms as known in the art implemented by the rate detection circuitry 310. Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as by use of the approaches disclosed in U.S. Pat. Nos. 5,545,186; 5,855,593; 6,141,581; 6,259,947; and 6,487,443, which are hereby incorporated herein by reference.

The detection circuitry 302, which is coupled to a microprocessor 306, may be configured to incorporate, or communicate with, specialized circuitry for processing sensed cardiac signals in manners particularly useful in a transthoracic cardiac sensing and/or stimulation device. As is shown by way of example in FIG. 1D, the detection circuitry 302 may receive information from multiple physiologic and non-physiologic sensors. Transthoracic acoustics, for example, may be monitored using an appropriate acoustic sensor. Heart sounds, for example, may be detected and processed by non-electrophysiologic cardiac sensor processing circuitry 318 for a variety of purposes. The acoustics data is transmitted to the detection circuitry 302, via a hardwire or wireless link, and used to enhance cardiac signal detection and/or arrhythmia detection. For example, acoustic information may be used in accordance with the present invention to corroborate ECG rate-based discrimination of arrhythmias.

The detection circuitry 302 may also receive information from one or more sensors that monitor skeletal muscle activity. In addition to cardiac activity signals, transthoracic electrodes readily detect skeletal muscle signals. Such skeletal muscle signals may be used to determine the activity level of the patient. In the context of cardiac signal detection, such skeletal muscle signals are considered artifacts of the cardiac activity signal, which may be viewed as noise. Processing circuitry 316 receives signals from one or more skeletal muscle sensors, and transmits processed skeletal muscle signal data to the detection circuitry 302. This data may be used to discriminate normal cardiac sinus rhythm with skeletal muscle noise from cardiac arrhythmias.

As was previously discussed, the detection circuitry 302 is coupled to, or otherwise incorporates, noise-processing circuitry 314. The noise processing circuitry 314 processes sensed cardiac signals to improve the signal-to-noise ratio of sensed cardiac signals by reducing noise content of the sensed cardiac signals.

The components, functionality, and structural configurations depicted in FIGS. 1A-1D are intended to provide an understanding of various features and combination of features that may be incorporated in an ITCS device or a patient-external system according to certain embodiments. It is understood that a wide variety of ITCS and other implantable and external cardiac monitoring and/or stimulation device configurations are contemplated, ranging from relatively sophisticated to relatively simple designs. As such, particular ITCS or external cardiac monitoring and/or stimulation device configurations may include particular features as described herein, while other such device configurations may exclude particular features described herein.

In accordance with embodiments of the invention, an ITCS device may be implemented to include a subcutaneous electrode system that provides for one or both of cardiac sensing and arrhythmia therapy delivery. According to one approach, an ITCS device may be implemented as a chronically implantable system that performs monitoring, diagnostic and/or therapeutic functions. The ITCS device may automatically detect and treat cardiac arrhythmias.

In one configuration, an ITCS device includes a pulse generator and one or more electrodes that are implanted subcutaneously in the chest region of the body, such as in the anterior thoracic region of the body. The ITCS device may be used to provide atrial and/or ventricular therapy for bradycardia, tachycardia, and asystole. Tachyarrhythmia therapy may include cardioversion, defibrillation, and anti-tachycardia pacing (ATP), for example, to treat atrial or ventricular tachycardia or fibrillation. Bradycardia therapy may include one or more known bradycardia pacing therapies. Methods and systems for implementing asystole prevention therapy that are particularly well suited for subcutaneous applications are described in commonly owned U.S. patent application Ser. No. 10/377,274, filed on Feb. 28, 2003, now U.S. Publication No. 2004/0172066, which is incorporated herein by reference in its entirety.

In one configuration, an ITCS device according to one approach may utilize conventional pulse generator and subcutaneous electrode implant techniques. The pulse generator device and electrodes may be chronically implanted subcutaneously. Such an ITCS device may be used to automatically detect and treat arrhythmias similarly to conventional implantable systems. In another configuration, the ITCS device may include a unitary structure (e.g., a single housing/unit). The electronic components and electrode conductors/connectors are disposed within or on the unitary ITCS device housing/electrode support assembly.

The ITCS device contains the electronics and may be similar to a conventional implantable defibrillator. High voltage shock therapy may be delivered between two or more electrodes, one of which may be the pulse generator housing (e.g., can), placed subcutaneously in the thoracic region of the body.

Additionally or alternatively, the ITCS device may also provide lower energy electrical stimulation for bradycardia therapy. The ITCS device may provide bradycardia pacing in a manner similar to pacing therapies deliverable by conventional pacemakers. The ITCS device may provide temporary post-shock pacing for bradycardia or asystole. Sensing and/or pacing may be accomplished using sense/pace electrodes positioned on an electrode subsystem also incorporating shock electrodes, or by separate electrodes implanted subcutaneously.

The ITCS device may detect a variety of physiological signals that may be used in connection with various diagnostic, therapeutic or monitoring implementations in accordance with the present invention. For example, the ITCS device may include sensors or circuitry for detecting pulse pressure signals, blood oxygen level, heart sounds, cardiac acceleration, and other non-electrophysiological signals related to cardiac activity. In one embodiment, the ITCS device senses intrathoracic impedance, from which various respiratory parameters and respiratory patterns may be derived, including, for example, respiratory tidal volume and minute ventilation. For example, an ITCS device may analyze respiratory parameters and/or patterns to detect disordered breathing, such as sleep apnea. In response to detecting sleep apnea, for example, the ITCS device may deliver a therapy to treat the detected sleep apnea, such as by delivering an appropriate pacing or other cardiac stimulation therapy (e.g., overdrive pacing). Sensors and associated circuitry may be incorporated in connection with an ITCS device for detecting one or more body movement or body position related signals. For example, accelerometers and GPS devices may be employed to detect patient activity, patient location, body orientation, or torso position.

The ITCS device may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

An ITCS device according to one approach provides an easy to implant therapeutic, diagnostic or monitoring system. The ITCS system may be implanted without the need for intravenous or intrathoracic access, providing a simpler, less invasive implant procedure and minimizing lead and surgical complications. In addition, this system would have advantages for use in patients for whom transvenous lead systems cause complications. Such complications include, but are not limited to, surgical complications, infection, insufficient vessel patency, complications associated with the presence of artificial valves, and limitations in pediatric patients due to patient growth, among others. An ITCS system according to this approach is distinct from conventional approaches in that it may be configured to include a combination of two or more electrode subsystems that are implanted subcutaneously in the anterior thorax.

Figure 2A:
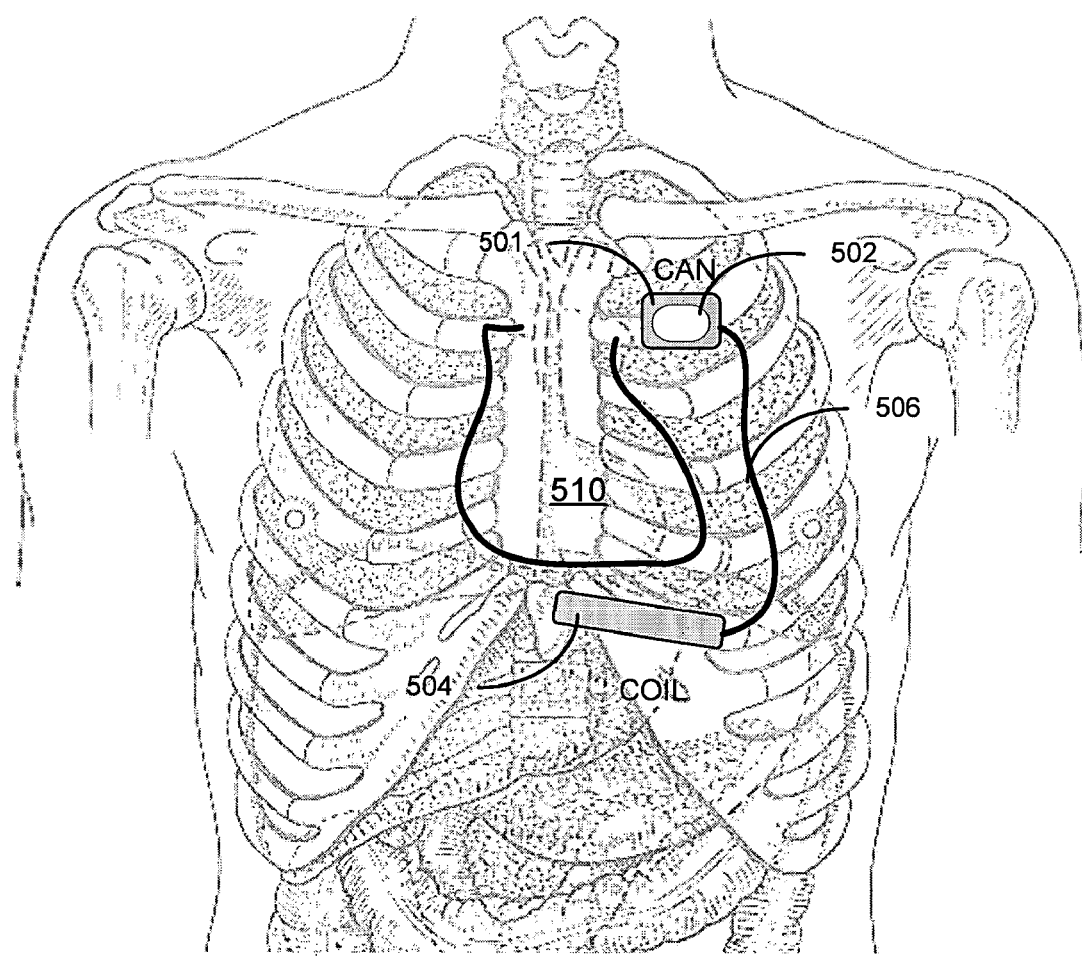
FIGS. 2A-2C are diagrams illustrating various components of a transthoracic cardiac sensing and/or stimulation device located in accordance with embodiments of the present invention.

In one configuration, illustrated in FIG. 2A, electrode subsystems of the ITCS system include a first electrode subsystem, comprising a can electrode 502, and a second electrode subsystem 504 that may include at least one coil electrode, for example. The second electrode subsystem 504 may include a number of electrodes used for sensing and/or electrical stimulation. In various configurations, the second electrode subsystem 504 may include a single electrode or a combination of electrodes. The single electrode or combination of electrodes comprising the second electrode subsystem 504 may include coil electrodes, tip electrodes, ring electrodes, multi-element coils, spiral coils, spiral coils mounted on non-conductive backing, and screen patch electrodes, for example. A suitable non-conductive backing material is silicone rubber, for example.

The can electrode 502 is located on the housing 501 that encloses the ITCS device electronics. In one embodiment, the can electrode 502 includes the entirety of the external surface of housing 501. In other embodiments, various portions of the housing 501 may be electrically isolated from the can electrode 502 or from tissue. For example, the active area of the can electrode 502 may include all or a portion of either the anterior or posterior surface of the housing 501 to direct current flow in a manner advantageous for cardiac sensing and/or stimulation. In certain implementations, multiple electrodes may be provided on or in the housing 501, such electrodes configured for sensing and/or energy delivery (e.g., pacing or defibrillation).

The housing 501 may resemble that of a conventional implantable ICD, is approximately 20-100 cc in volume, with a thickness of 0.4 to 2 cm and with a surface area on each face of approximately 30 to 100 cm². As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

FIG. 2A illustrates the housing 501 and can electrode 502 placed subcutaneously, superior to the heart 510 in the left pectoral region, which is a location commonly used for conventional pacemaker and defibrillator implants. The second electrode subsystem 504 may include a coil electrode mounted on the distal end of a lead body 506, where the coil is approximately 3-15 French in diameter and 5-12 cm in length. The coil electrode may have a slight preformed curve along its length. The lead may be introduced through the lumen of a subcutaneous sheath, through a common tunneling implant technique, and the second electrode subsystem 504, e.g., comprising a coil electrode, may be placed subcutaneously, deep to any subcutaneous fat and adjacent to the underlying muscle layer.

In this configuration, the second electrode subsystem 504 is located approximately parallel with the inferior aspect of the right ventricle of the heart 510, just inferior to the right ventricular free wall, with one end extending just past the apex of the heart 510. For example, the tip of the electrode subsystem 504 may extend less than about 3 cm and may be about 1-2 cm left lateral to the apex of the heart 510. By way of further example, an electrode subsystem 504 implemented as a coil may have a length of about 5 cm, with about 3 cm of the coil situated left lateral of the apex and about 2 cm of the coil situated right lateral of the apex. These electrode arrangements may be used to include a majority of ventricular tissue within a volume defined between the housing 501 and the second electrode subsystem 504. In one configuration, a majority of the ventricular tissue is included within a volume associated with an area bounded by planes defined between the distal and proximal ends of the second electrode subsystem 504 and the medial and lateral edges of the left pectoral can electrode 502.

In one example arrangement, the volume including a majority of ventricular tissue may be associated with a cross sectional area bounded by lines or planes defined between the ends of the electrode subsystems 502, 504 or between active elements of the electrode subsystems 502, 504. In one implementation, the planes defined between active elements of the electrode subsystems 502, 504 may include a medial edge and a lateral edge of the can electrode 502, and a proximal end and a distal end of a coil electrode utilized within the second electrode subsystem 504. Arranging the electrode subsystems so that a majority of ventricular tissue is contained within a volume defined between the active elements of the electrode subsystems 502, 504 provides an efficient position for defibrillation by increasing the voltage gradient in the ventricles of the heart 510 for a given applied voltage between electrode subsystems 502, 504. Additional details concerning subcutaneous electrode positioning according to embodiments of the present invention are disclosed in previously incorporated U.S. patent application Ser. No. 10/465,520, filed Jun. 19, 2003, now U.S. Publication No. 2004/0230230.

Figure 2B:
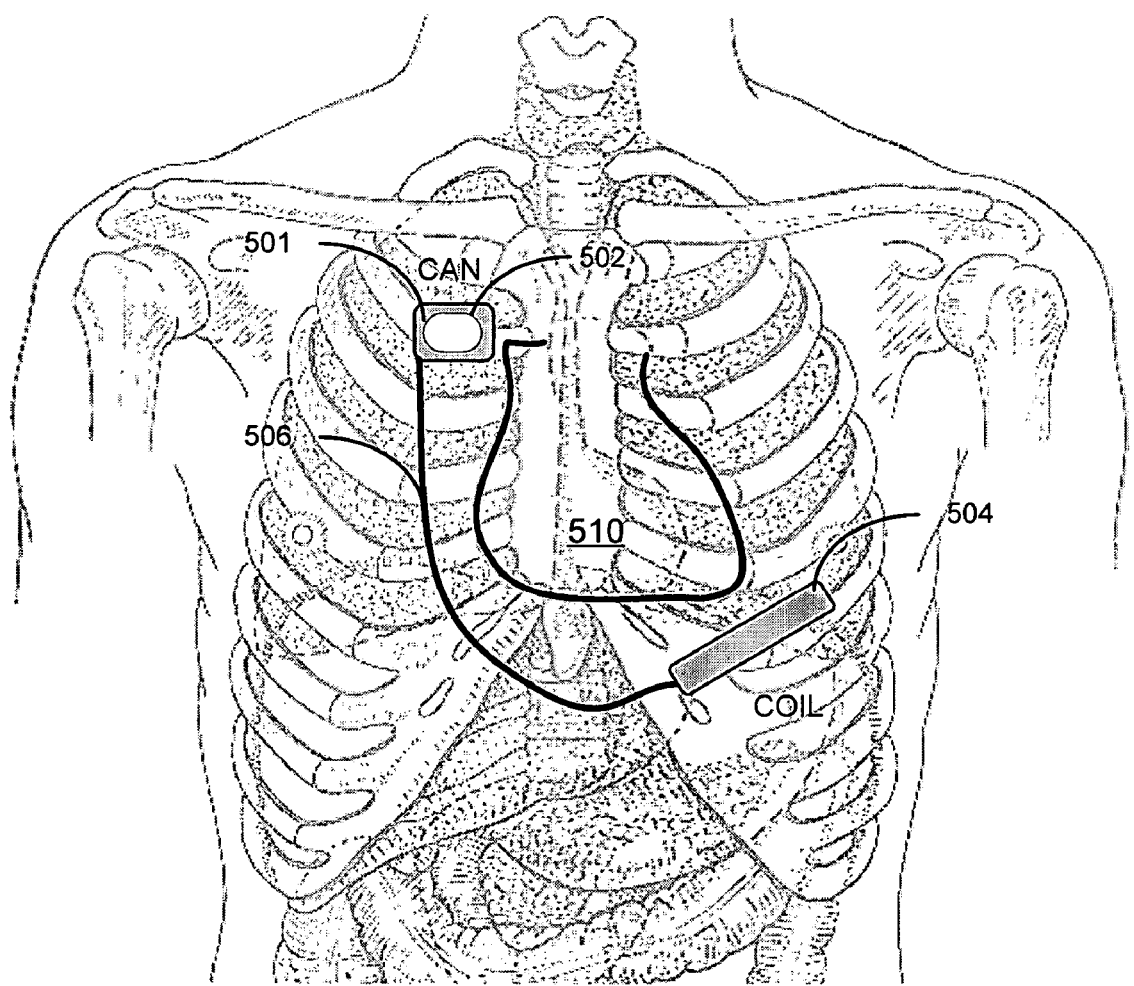

In a similar configuration, and as shown in FIG. 2B, the housing 501 comprising the can electrode 502 is placed in the right pectoral region. The second electrode subsystem 504 is located more laterally, to again include a majority of the ventricular tissue in a volume defined between the can electrode 502 and the second electrode subsystem 504.

Figure 2C:
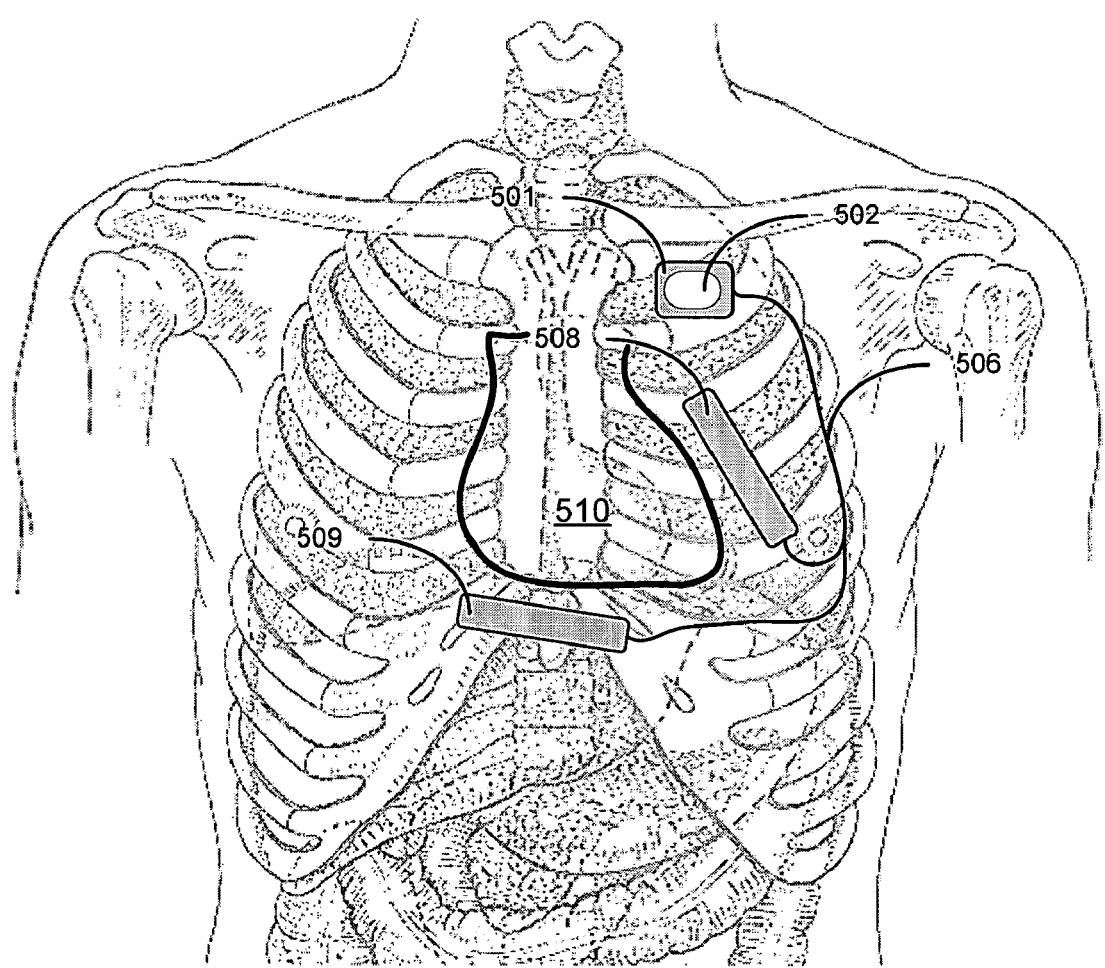

In a further configuration, and as shown in FIG. 2C, the ITCS device housing 501 containing the electronics (i.e., the can) is not used as an electrode. In this case, an electrode system comprising two electrode subsystems 508, 509 coupled to the housing 501 may be implanted subcutaneously in the chest region of the body, such as in the anterior thorax. The first and the second electrode subsystems 508, 509 are placed in opposition with respect to the ventricles of the heart 510, with the majority of the ventricular tissue of the heart 510 included within a volume defined between the electrode subsystems 508, 509. As illustrated in FIG. 2C, the first electrode system 508 is located superior to the heart 510 relative to a superior aspect of the heart 510, e.g., parallel to the left ventricular free wall. The second electrode system 509 is located inferior to the heart 510 and positioned in relation to an inferior aspect of the heart 510, e.g., parallel to the right ventricular free wall.

In this configuration, the first and the second electrode subsystems 508, 509 may include any combination of electrodes, including or excluding the can electrode, used for sensing and/or electrical stimulation. In various configurations, the electrode subsystems 508, 509 may each be a single electrode or a combination of electrodes. The electrode or electrodes comprising the first and second electrode subsystems 508, 509 may include any combination of one or more coil electrodes, tip electrodes, ring electrodes, multielement coils, spiral coils, spiral coils mounted on non-conductive backing, and screen patch electrodes, for example.

Figure 3A:
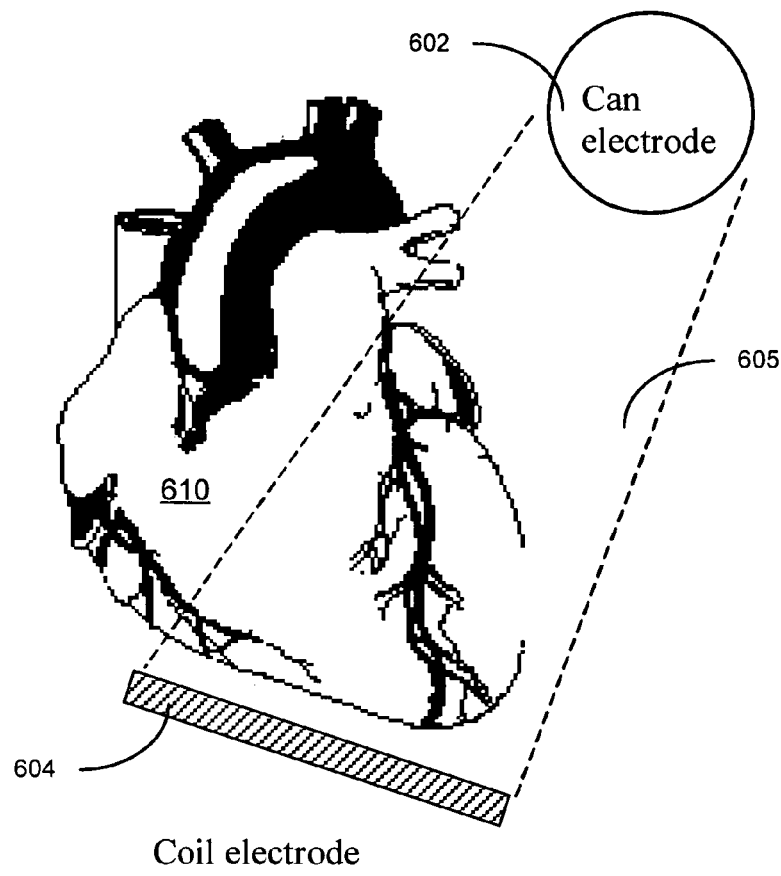
FIGS. 3A-3C are diagrams illustrating electrode subsystem placement relative to a heart in accordance with embodiments of the present invention.
Figure 3B:
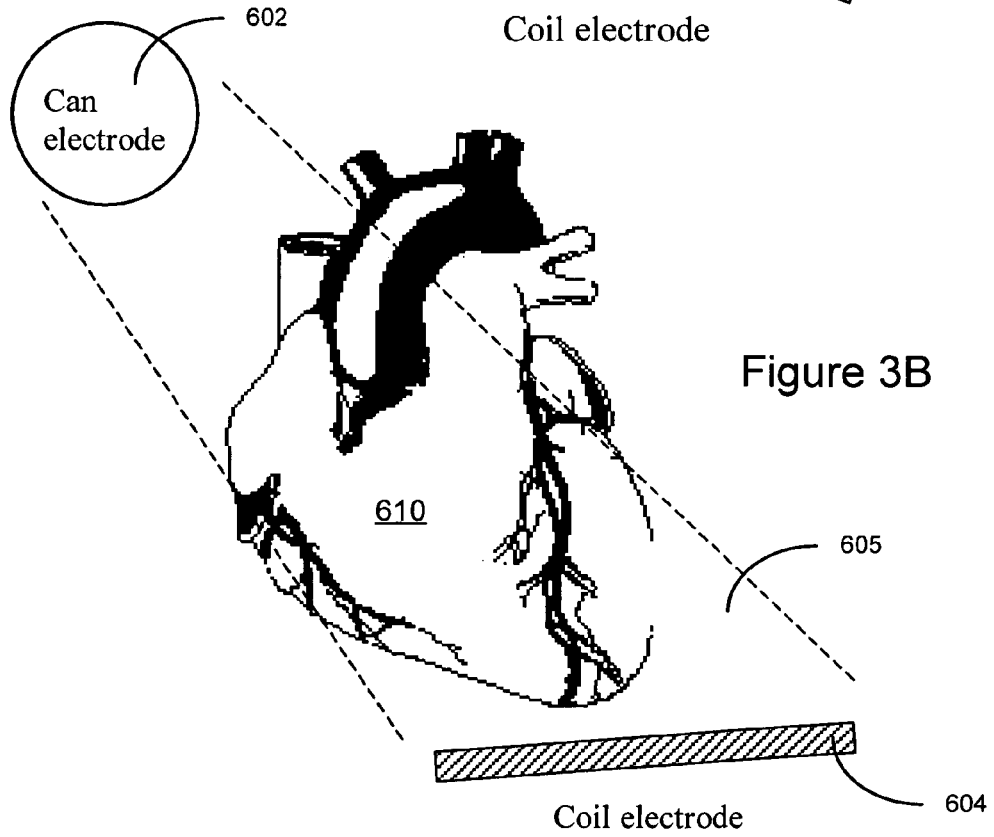
Figure 3C:
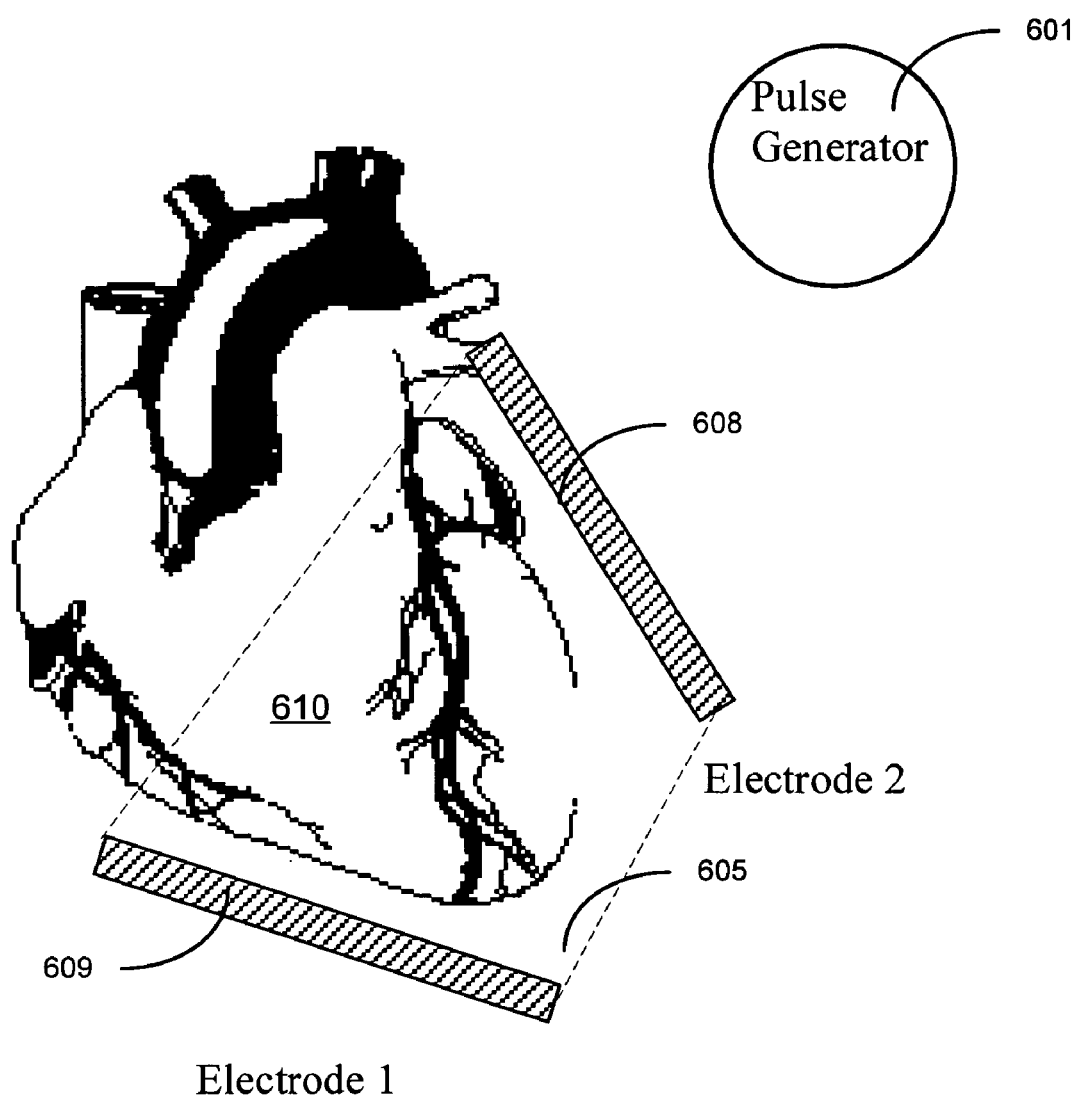

FIGS. 3A-3C provide additional detailed views of subcutaneous electrode subsystem placement considered particularly useful in patient implant stratification in accordance with embodiments of the present invention. FIG. 3A illustrates first and second electrode subsystems configured as a can electrode 602 and a coil electrode 604, respectively. FIG. 3A illustrates the can electrode 602 located superior to the heart 610 in the left pectoral region and the coil electrode 604 located inferior to the heart 610, parallel to the right ventricular free wall of the heart 610.

The can electrode 602 and the coil electrode 604 are located so that the majority of ventricular tissue is included within a volume defined between the can electrode 602 and the coil electrode 604. FIG. 3A illustrates a cross sectional area 605 formed by the planes defined between active elements of the can electrode 602 and the coil electrode 604. Planes defined between active areas of the electrodes 602, 604 may be defined by a medial edge and a lateral edge of the can electrode 602, and a proximal end and a distal end of a coil electrode utilized as the second electrode subsystem 604. The coil electrode 604 extends a predetermined distance beyond the apex of the heart 610, e.g. less than about 3 cm. In another configuration, the coil electrode 604 may have a length of about 5 cm, with about 3 cm of the coil electrode 604 situated left lateral of the apex and about 2 cm of the coil electrode 604 situated right lateral of the apex.

A similar configuration is illustrated in FIG. 3B. In this embodiment, the can electrode 602 is placed superior to the heart 610 in the right pectoral region. The coil electrode 604 is located inferior to the heart. In one arrangement, the coil electrode is located relative to an inferior aspect of the heart 610, for example, the apex of the heart. The can electrode 602 and the coil electrode 604 are positioned so that the majority of ventricular tissue is included within a volume defined between the can electrode 602 and the coil electrode 604.

FIG. 3B illustrates a cross sectional area 605 formed by the planes defined between active elements of the can electrode 602 and the coil electrode 604. Planes defined between active areas of the electrodes 602, 604 may be defined by a medial edge and a lateral edge of the can electrode 602, and a proximal end and a distal end of a coil electrode utilized as the second electrode subsystem 604. The coil electrode 604 extends a predetermined distance beyond the apex of the heart 610, e.g. less than about 3 cm. As discussed above with regard to FIG. 3A, the coil electrode 604 may have a length of about 5 cm, with about 3 cm of the coil electrode 604 situated left lateral of the apex and about 2 cm of the coil electrode 604 situated right lateral of the apex.

FIG. 3C illustrates a configuration wherein the pulse generator housing 601 does not include an electrode. In this implementation two electrode subsystems are positioned about the heart so that a majority of ventricular tissue is included within a volume defined between the electrode subsystems. According to this embodiment, the first and second electrodes are configured as first and second coil electrodes 608, 609. The first coil electrode 608 is located superior to the heart 610 and may be located relative to a superior aspect of the heart, e.g., the left ventricular free wall. The second coil electrode 609 is located inferior to the heart 610. The second electrode 609 may be located in relation to an inferior aspect of the heart 610. In one configuration, the second electrode 609 is positioned parallel to the right ventricular free wall with a tip of the electrode 609 extending less than about 3 cm beyond the apex of the heart 610. In another configuration, as discussed above, the second electrode 609 may have a length of about 5 cm, with about 3 cm of the second electrode 609 situated left lateral of the apex and about 2 cm of the second electrode 609 situated right lateral of the apex. As illustrated in FIG. 3C, the volume defined between the electrodes may be characterized by the cross sectional area 605 bounded by planes defined between active areas of the electrodes 608, 609.

Figure 4:
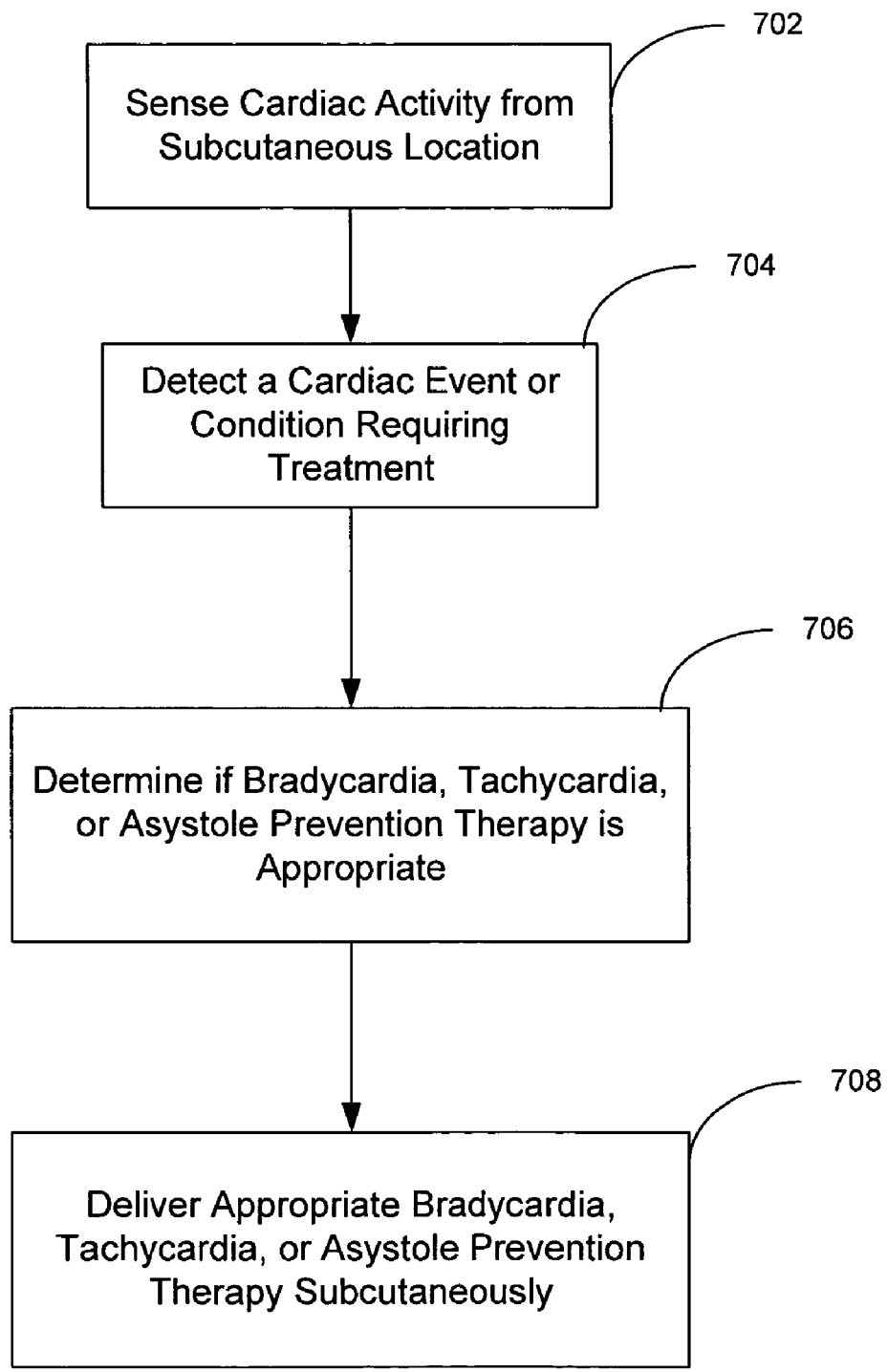
FIG. 4 is a flow diagram describing various processes of a cardiac sensing and energy delivery approach in accordance with an embodiment of the present invention.

FIG. 4 is a flow chart illustrating a cardiac detection and therapy delivery approach in accordance with an embodiment of the present invention. According to this embodiment, cardiac activity is sensed 702 from a subcutaneous location. A cardiac condition or event that requires treatment is detected 704. Detection of the cardiac condition or event may be performed at a subcutaneous location or a location external to the patient. A determination is made 706 as to which of several available therapies is appropriate to treat the detected cardiac condition or event. This determination 706 may be made at a subcutaneous location or a location external to the patient.

By way of example, and as shown in the particular embodiment depicted in FIG. 4, the available cardiac therapies may include a tachycardia therapy, including defibrillation therapy, a bradycardia therapy, and an asystole prevention therapy. The appropriate therapy (or therapies) is delivered 708, such as a tachycardia, bradycardia, or asystole prevention therapy, for example. The energy waveform(s) associated with the delivered therapy may be generated at a subcutaneous location or a location external to the patient.

In accordance with one embodiment of an asystole prevention therapy, an ITCS device can be programmed to detect cardiac asystole subsequent to delivery of a defibrillation therapy and, in response, deliver a life sustaining, non-physiologic transthoracic pacing therapy to terminate the detected cardiac asystole. The pacing therapy provides for delivery of pacing pulses at a rate substantially lower than a bradycardia pacing rate. The pacing therapy can involve delivery of pacing pulses at a progressively increasing rate, a progressively decreasing rate or at a substantially constant rate for all or a predetermined duration of the therapy. For example, a given pacing interval can be increased by a fixed amount or a certain percentage relative to a preceding pacing interval. The pacing therapy can alternatively involve delivery of a series of pacing pulses, where the series of pacing pulses includes at least one sequence delivered at a variable rate and at least one sequence delivered at a substantially constant rate.

Pacing, in this regard, is provided only as a means to maintain patient life post shock during asystole. The maximum pacing interval is preferably short enough to maintain life, but sufficiently long enough to not enable full consciousness in the patient where pacing could be perceived as particularly painful. A suitable pacing rate typically ranges between 2 and 40 pulses per minute (ppm), with 5-20 ppm representing a typical pacing rate. The pacing electrodes may be the same as the shock electrodes or can include one or more dedicated pacing electrodes.

Figure 5:
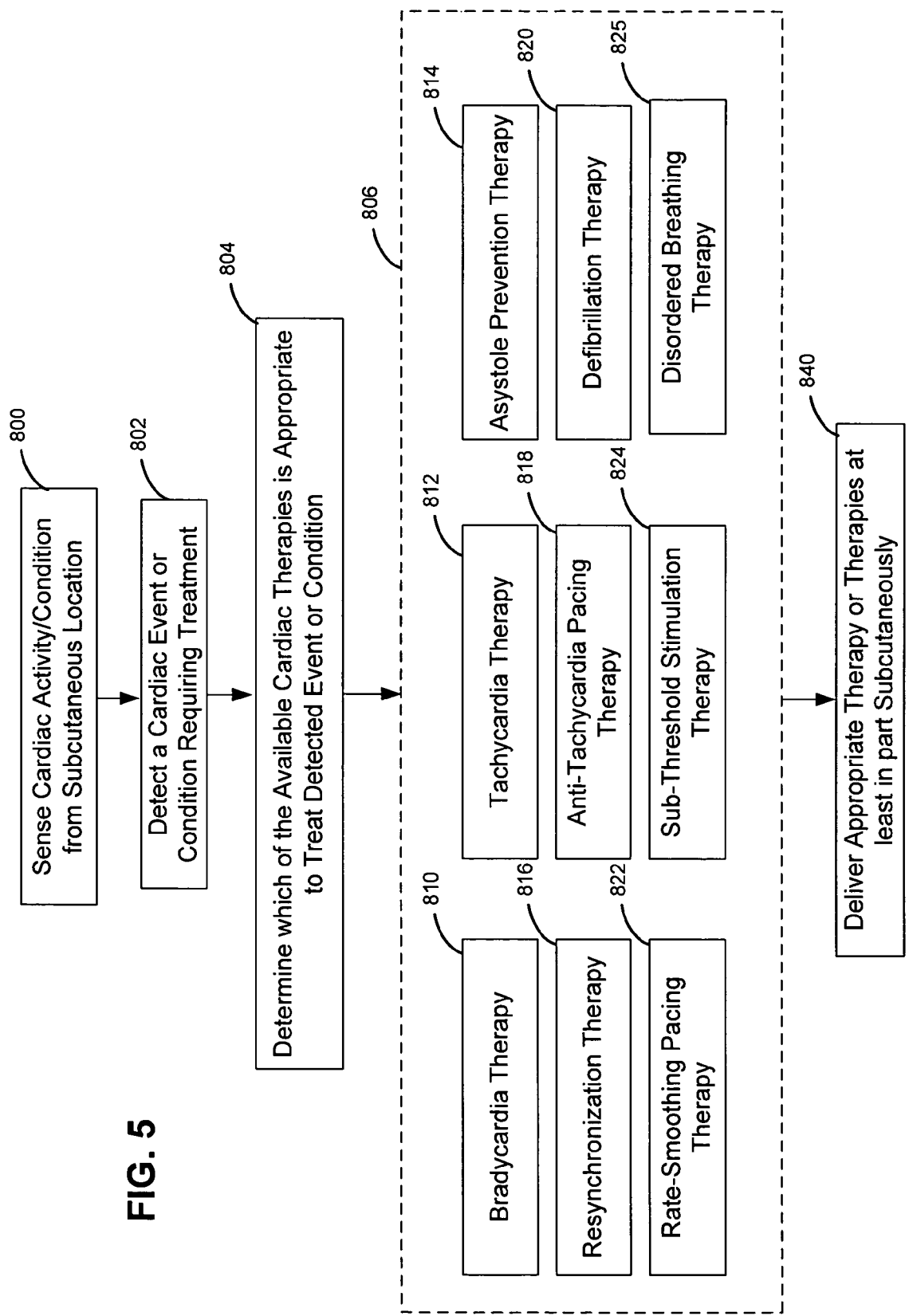
FIG. 5 is a flow diagram describing various processes of a cardiac sensing and energy delivery approach in accordance with another embodiment of the present invention.

FIG. 5 is a flow chart illustrating a cardiac detection and therapy delivery approach in accordance with another embodiment of the present invention. According to this embodiment, cardiac activity is sensed 800 from a subcutaneous location. A cardiac condition or event that requires treatment is detected 802. As in the previous embodiment, detection of the cardiac condition or event may be performed at a subcutaneous location or a location external to the patient. A determination is made 804 as to which of several available therapies is appropriate to treat the detected cardiac condition or event, which may be made at a subcutaneous location or a location external to the patient.

In the particular embodiment shown in FIG. 5, the available cardiac therapies 806 include, in general, bradycardia therapies 810, tachycardia therapies 812, asystole prevention therapies 814, and, in particular, resynchronization therapies 816, anti-tachycardia pacing therapies (ATP) 818, defibrillation therapies 820, rate smoothing or regularization therapies 822, sub-threshold stimulation therapies 824, or disordered breathing therapies 825. The appropriate therapy or therapies is/are delivered 840 at least in part implantably. The energy waveform(s) associated with the delivered therapy 840 may be generated at a subcutaneous location or a location external to the patient. The therapies depicted in FIG. 5 may be implemented in accordance with those previously described or those incorporated herein by reference.

Figure 6:
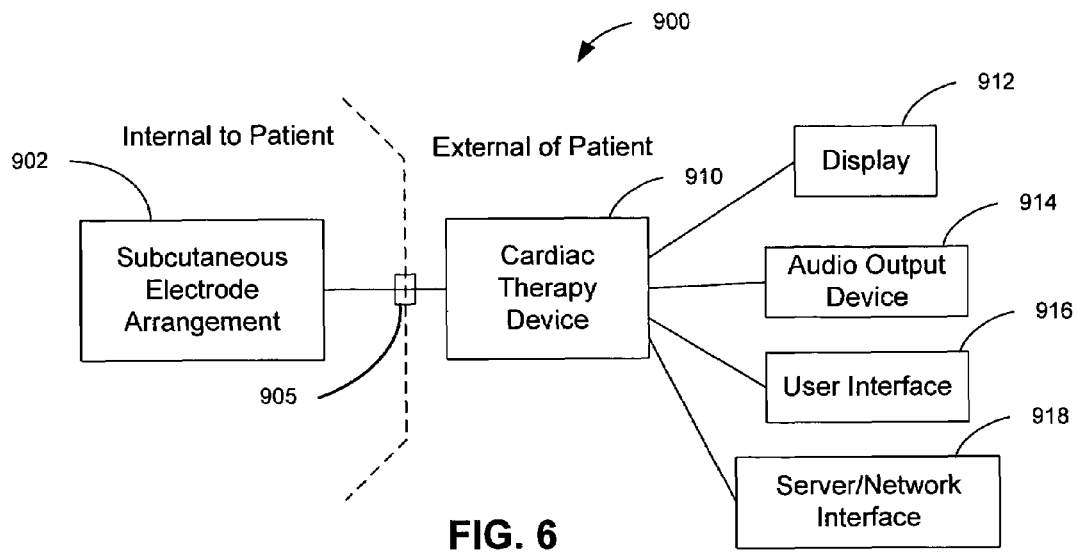
FIG. 6 is a block diagram of various components of a cardiac detection and therapy delivery system in accordance with an embodiment of the present invention.

FIG. 6 is a block diagram of various components of a cardiac detection and therapy delivery system in accordance with an embodiment of the present invention. As is shown in FIG. 6, the system 900 includes an electrode arrangement configured for implantation in a patient. The system 900 also includes components that are external to the patient. In particular, the system 900 of FIG. 6 includes at least one electrode arrangement 902 configured for subcutaneous, non-intrathoracic placement in the body. The patient-external components of the system 900 include a cardiac therapy device 910, which includes detection circuitry and energy delivery circuitry for respectively detecting cardiac activity and delivering various cardiac therapies as previously described. The cardiac therapy device 910 is coupled to the subcutaneous electrode arrangement 902 by a suitable connection interface 905. The connection interface 905 is preferably configured to facilitate connection and disconnection as between the cardiac therapy device 910 and conductors of the subcutaneous electrode arrangement 902.

In FIG. 6, various components are shown coupled to the cardiac therapy device, it being understood that fewer, more, or different components may be coupled to the cardiac therapy device 910. It is further understood that the various components shown as separate component blocks in FIG. 6 may instead represent functional features of a patient-external system that incorporates such functions. A display 912 is shown coupled to the cardiac therapy device 910, which facilitates presentation of various types and forms of data (e.g., textual and/or graphical) for viewing by the patient, care-giver or physician.

An audio output device 914 may also be coupled to the cardiac therapy device 910. Heart sounds may, for example, be broadcast to the patient, care-giver or physician via the audio output device 914. By way of example, heart sounds and cardiac electrophysiologic data may be broadcast and presented to the patient, care-giver or physician via the audio output device 914 and display 912 in accordance with the approaches described in commonly owned, co-pending U.S. patent application Ser. No. 10/801,139, filed Mar. 15, 2004, now U.S. Publication No. 2004/0230249, which is hereby incorporated herein by reference.

The external components of the system 900 may also include a user interface 916, which may take on a variety of forms. The user interface 916 may be implemented to have varying complexity, ranging from relatively complex capabilities (e.g., a programmer) to relatively simple capabilities (e.g., a bed-side console or patient activator device). The user interface 916 permits the patient, care-giver or physician to communicate, interrogate, and/or interact with the cardiac therapy device 910, depending on the sophistication of the user interface 916. For example, the user interface 916 may allow the patient to initiate recording of cardiac activity, much in the way of a loop recorder. Details of useful heart activity recording techniques are disclosed in commonly owned, co-pending U.S. patent application Ser. No. 10/785,431 filed Feb. 24, 2004, now U.S. Publication No. 2005/0004615, which is hereby incorporated herein by reference. By way of further example, a physician may interrogate and/or program the cardiac therapy device 910 via the user interface 916.

The system 900 may further include an interface 918 configured to facilitate communication between the cardiac therapy device 910 and other systems, such as a remote system, a network or server system, or other local or remote system. For example, the interface 918 may facilitate communications necessary to perform advanced patient management (APM) functions, such as those previously described or incorporated herein by reference.

Figure 7:
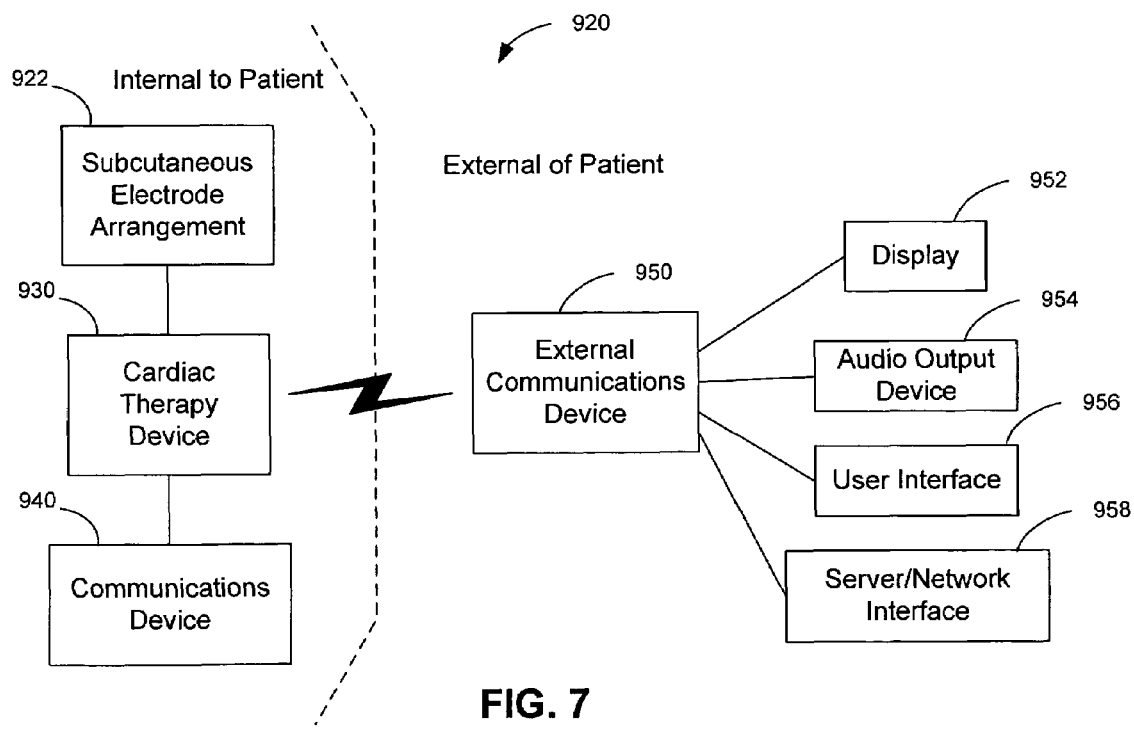
FIG. 7 is a block diagram of various components of a cardiac detection and therapy delivery system in accordance with another embodiment of the present invention.

FIG. 7 is a block diagram of various components of a cardiac detection and therapy delivery system in accordance with another embodiment of the present invention. As is shown in FIG. 7, the system 920 includes several patient-internal components and several patient-external components. According to this embodiment, the patient-internal and patient-external components communicate with one another via a wireless connection, such as conventional RF link, a Bluetooth link, a communication protocol conforming to IEEE 802 standards, or other form of communication link.

The patient-internal components of the system 920 include at least one electrode arrangement 922 configured for subcutaneous, non-intrathoracic placement in the body. In this embodiment, a cardiac therapy device 930, such as an ITCS device of a type previously described or incorporated herein by reference, is configured for subcutaneous, non-intrathoracic placement in the body and coupled to the subcutaneous electrode arrangement 922. The cardiac therapy device 930 includes detection circuitry and energy delivery circuitry for respectively detecting cardiac activity and delivering various cardiac therapies as previously described. A communications device 940 is provided internal to the patient, and coupled to or incorporated within the cardiac therapy device 930. The communications device 940 is configured to facilitate wireless communication with a communications device 950 of a patient-external system or device, such as in a manner previously discussed.

The subcutaneous electrode arrangement 922 may be implemented as multiple electrodes in or on a housing of the cardiac therapy device 930 (e.g., a unitary housing, such as an arcuate housing generally conforming to the shape of the patient's rib cage). The subcutaneous electrode arrangement 922 may be implemented as multiple electrode subsystems separate from the housing of the cardiac therapy device 930 and coupled thereto via a lead or support system. The subcutaneous electrode arrangement 922 may further be implemented as one or more housing electrodes and one or more electrode subsystems separate from the housing of the cardiac therapy device 930. The system 920 includes various other patient-external components which are shown coupled to the cardiac therapy device 930 via the external communications device 950. It is understood that fewer, more, or different components may be incorporated in a patient-external system that is communicatively coupled to the cardiac therapy device 930 via the external communications device 950.

In the embodiment shown in FIG. 7, the external communications device 950 is coupled to a display 952 that facilitates for visual presentation of various types and forms of data to the patient, care-giver or physician. The external communications device 950 may be coupled to an audio output device 954, a user interface 956, and an interface 958 configured to facilitate communication between the cardiac therapy device 950 and other systems, such as a remote system, a network or server system, or other local or remote system (e.g., APM systems). It is understood that the various components shown as separate component blocks in FIG. 7 may instead represent functional features of a patient-external system that incorporates such functions. It is further understood that the embodiments depicted in FIGS. 6 and 7 may incorporate other sensors, such as non-electrophysiologic sensors as previously described or incorporated by reference.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What we claim is:

1. A system, comprising:
   detection circuitry;
   energy delivery circuitry capable of delivering a plurality of cardiac therapies comprising at least a tachycardia therapy, a bradycardia therapy, and an asystole prevention therapy;
   therapy instructions stored in the energy delivery circuitry, the therapy instructions executable to direct delivery of the plurality of cardiac therapies;
   one or more electrodes configured for subcutaneous, non-intrathoracic placement in a patient and for coupling to the detection circuitry and energy delivery circuitry;
   detection circuitry configured to receive cardiac signals using the one or more electrodes and detect a tachycardia condition, a bradycardia condition, and an asystole condition using the cardiac signals;
   a controller coupled to the detection circuitry and energy delivery circuitry, the controller, in response to a cardiac condition requiring treatment, executing at least some of the therapy instructions to coordinate delivery of a selected one of the tachycardia, bradycardia, and asystole prevention therapies, the asystole prevention therapy being delivered at a rate below that of the bradycardia therapy and at 20 pulses per minute or less upon detection of the asystole condition;

a patient-external communications device configured to receive data relating to the selected one of the tachycardia, bradycardia, and asystole prevention therapies, wherein the patient-external communications device facilitates communication with a network or server system; and a display coupled to the patient-external communications device for displaying the received data.

2. The system of claim 1, wherein the plurality of cardiac therapies comprises a bradycardia pacing therapy.

3. The system of claim 1, wherein the plurality of cardiac therapies comprises a cardiac resynchronization therapy.

4. The system of claim 1, wherein the plurality of cardiac therapies comprises an antitachycardia pacing therapy.

5. The system of claim 1, wherein the plurality of cardiac therapies comprises a defibrillation therapy.

6. The system of claim 1, wherein the plurality of cardiac therapies comprises a rate smoothing pacing therapy.

7. The system of claim 1, wherein the plurality of cardiac therapies comprises a sub-threshold stimulation therapy.

8. The system of claim 1, wherein the one or more electrodes are configured for cardiac pacing and sensing.

9. The system of claim 1, further comprising a housing within which the detection circuitry, energy delivery circuitry, and controller are situated, wherein the housing is configured for patient-external placement.

10. The system of claim 9, wherein the housing comprises one or more electrodes coupled to the detection circuitry and energy delivery circuitry.

11. The system of claim 9, further comprising one or more surface electrodes configured for coupling to the detection circuitry and energy delivery circuitry.

12. The system of claim 9, further comprising a coupling arrangement configured to couple and de-couple the one or more electrodes to and from the detection circuitry and energy delivery circuitry.

13. The system of claim 1, further comprising a housing within which at least one of the detection circuitry, energy delivery circuitry, and controller is situated, wherein the housing is configured for implantation in a patient.

14. The system of claim 13, wherein the one or more electrodes comprises at least one electrode disposed in or on the housing.

15. The system of claim 1, wherein the asystole prevention therapy comprises delivery of no more than ten pacing pulses.

16. The system of claim 1, wherein the asystole prevention therapy comprises delivery of pacing pulses at a rate insufficient to restore full patient consciousness.

17. The system of claim 1, wherein the rate below that of the bradycardia therapy is a fixed rate or a variable rate.

18. The system of claim 1, further comprising a housing within which the detection circuitry, energy delivery circuitry, and controller are situated, wherein the housing is configured for implantation in a patient and the one or more electrodes are disposed in or on the housing to define a unitary structure.

19. The system of claim 18, wherein the housing is configured to have an arcuate shape.

20. A system, comprising:

a housing configured for subcutaneous, non-intrathoracic placement relative to a patient;

energy delivery circuitry provided in the housing and capable of delivering each of a tachycardia therapy, a bradycardia therapy, and an asystole prevention therapy;

therapy instructions stored in the energy delivery circuitry, the therapy instructions executable to direct delivery of the tachycardia therapy, the bradycardia therapy, and the asystole prevention therapy, the asystole prevention therapy comprising a pacing rate lower than that associated with the bradycardia therapy and 20 pulses per minute or less;

one or more electrodes configured for subcutaneous, non-intrathoracic placement and coupled to the detection circuitry and energy delivery circuitry;

detection circuitry provided in the housing and configured to receive cardiac signals using the one or more electrodes and to detect a tachycardia condition, a bradycardia condition, and an asystole condition using the cardiac signals;

a controller provided in the housing and coupled to the detection circuitry and energy delivery circuitry, the controller, in response to a cardiac condition requiring treatment, executing at least some of the therapy instructions to direct delivery of a selected one of the tachycardia, bradycardia, and asystole prevention therapies in response to detection of a corresponding one of the tachycardia condition, the bradycardia condition, and the asystole condition, respectively;

a patient-external communications device configured to receive data relating to the selected one of the tachycardia, bradycardia, and asystole prevention therapies, wherein the patient-external communications device facilitates communication with a network or server system; and a display coupled to the patient-external communications device for displaying the received data.

21. The system of claim 20, wherein the bradycardia therapy comprises a bradycardia pacing therapy.

22. The system of claim 20, wherein the therapy instructions are executable to direct delivery of a cardiac resynchronization therapy.

23. The system of claim 20, wherein the therapy instructions are executable to direct delivery of an antitachycardia pacing therapy.

24. The system of claim 20, wherein the therapy instructions are executable to direct delivery of a defibrillation therapy.

25. The system of claim 20, wherein the therapy instructions are executable to direct delivery of a rate smoothing pacing therapy.

26. The system of claim 20, wherein the therapy instructions are executable to direct delivery of a sub-threshold stimulation therapy.

27. The system of claim 20, wherein the one or more electrodes are configured for cardiac pacing and sensing.

28. The system of claim 20, wherein the one or more electrodes comprises at least one electrode disposed in or on the housing.

29. The system of claim 20, wherein the asystole prevention therapy delivered by the energy delivery circuitry comprises delivery of pacing pulses at a rate insufficient to restore full patient consciousness.

30. The system of claim 20, wherein the asystole prevention therapy delivered by the energy delivery circuitry comprises delivery of no more than ten pacing pulses.

31. The system of claim 30, wherein the rate lower than the pacing rate is a fixed rate or a variable rate.

32. The system of claim 20, wherein the one or more electrodes are disposed in or on the housing to define a unitary structure.

33. The system of claim 32, wherein the housing is configured to have an arcuate shape.

34. The system of claim 20, wherein the one or more electrodes comprise at least one subcutaneous, non-intrathoracic electrode array.

35. The system of claim 34, wherein the at least one subcutaneous, non-intrathoracic electrode array is coupled to the housing via a lead.

36. A method, comprising:
sensing cardiac activity from a subcutaneous, non-intrathoracic location of a patient;
detecting one of a plurality of cardiac conditions, each cardiac condition necessitating treatment in response to the sensed cardiac activity, the plurality of cardiac conditions comprising a tachycardia condition, a bradycardia condition, and an asystole condition;
delivering, in response to detecting a corresponding one of the plurality of cardiac conditions, one of a plurality of available cardiac therapies to treat the detected corresponding cardiac condition, the plurality of cardiac therapies comprising at least a tachycardia therapy, a bradycardia therapy, and an asystole prevention therapy, the asystole prevention therapy comprising a pacing rate lower than that associated with the bradycardia therapy and 20 pulses per minute or less;
transmitting data relating to the delivered one of the tachycardia, bradycardia, and asystole prevention therapies to a patient-external communications device, wherein the patient-external communications device facilitates communication with a network or server system; and
displaying the data transmitted to the patient-external communications device.

37. The method of claim 36, wherein the plurality of cardiac therapies comprises a bradycardia pacing therapy.

38. The method of claim 36, wherein the plurality of cardiac therapies comprises a cardiac resynchronization pacing therapy.

39. The method of claim 36, wherein the plurality of cardiac therapies comprises an antitachycardia pacing therapy.

40. The method of claim 36, wherein the plurality of cardiac therapies comprises a defibrillation therapy.

41. The method of claim 36, wherein the plurality of cardiac therapies comprises a rate smoothing pacing therapy.

42. The method of claim 36, wherein the plurality of cardiac therapies comprises a sub-threshold stimulation therapy.

43. The method of claim 36, wherein detecting comprises detecting the one of the plurality of cardiac conditions at a subcutaneous, non-intrathoracic location.

44. The method of claim 36, wherein detecting comprises detecting the cardiac condition at a patient-external location.

45. The method of claim 36, wherein energy for the plurality of cardiac therapies is provided from a patient-external source.

46. The method of claim 36, wherein energy for the plurality of cardiac therapies is provided from a subcutaneous, non-intrathoracic source.

47. The method of claim 36, wherein delivering the plurality of cardiac therapies comprises delivering monophasic waveforms.

48. The method of claim 36, wherein delivering the plurality of cardiac therapies comprises delivering multiphasic waveforms.

49. A system, comprising:
means for sensing cardiac activity from a subcutaneous, non-intrathoracic location of a patient;
means for detecting one of a plurality of cardiac conditions, each cardiac condition necessitating treatment in response to the sensed cardiac activity, the plurality of cardiac conditions comprising a tachycardia condition, a bradycardia condition, and an asystole condition;
means for delivering, in response to detecting a corresponding one of the plurality of cardiac conditions, one of a plurality of cardiac therapies to treat the detected corresponding cardiac condition, the plurality of cardiac therapies comprising at least a tachycardia therapy, a bradycardia therapy, and an asystole prevention therapy, all of which can be delivered by the system, the asystole prevention therapy comprising a pacing rate lower than that associated with the bradycardia therapy and 20 pulses per minute or less;
means for transmitting data relating to the delivered one of the tachycardia, bradycardia, and asystole prevention therapies to a patient-external communications device, wherein the patient-external communications device facilitates communication with a network or server system; and
means for displaying the data transmitted to the patient-external communications device.

50. The system of claim 49, wherein the plurality of cardiac therapies comprises a bradycardia pacing therapy.

51. The system of claim 49, wherein the plurality of cardiac therapies comprises a cardiac resynchronization pacing therapy.

52. The system of claim 49, wherein the plurality of cardiac therapies comprises an antitachycardia pacing therapy.

53. The system of claim 49, wherein the plurality of cardiac therapies comprises a defibrillation therapy.

54. The system of claim 49, wherein the plurality of cardiac therapies comprises a rate smoothing pacing therapy.

55. The system of claim 49, wherein the plurality of cardiac therapies comprises a sub-threshold stimulation therapy.

56. The system of claim 49, wherein the detecting means comprises means for detecting the one of the plurality of cardiac conditions at a subcutaneous, non-intrathoracic location.

57. The system of claim 49, wherein the detecting means comprises means for detecting the cardiac condition at a patient-external location.

58. The system of claim 49, further comprising means for supplying energy for the plurality of cardiac therapies from a patient-external source.

59. The system of claim 49, further comprising means for supplying energy for the plurality of cardiac therapies from a subcutaneous, non-intrathoracic source.

60. The system of claim 49, wherein the delivering means comprises means for delivering monophasic waveforms.

61. The system of claim 49, wherein the delivering means comprises means for delivering multiphasic waveforms.

* * * * *